(12) United States Patent
Osswald et al.

(10) Patent No.: US 7,491,521 B2
(45) Date of Patent: Feb. 17, 2009

(54) RHODOCOCCUS NITRILE HYDRATASE

(75) Inventors: Steffen Osswald, Rodenbach (DE);
Stefan Verseck, Hanau (DE); Uta Deiting, Frankfurt (DE); Christoph Weckbecker, Gründau-Lieblos (DE); Klaus Huthmacher, Gelnhausen (DE); Michael Binder, Hasselroth-Niedermittlau (DE); Maria-Regina Kula, München (DE); Konrad Odendahl, Köln (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 11/892,085

(22) Filed: Aug. 20, 2007

(65) Prior Publication Data

US 2008/0057549 A1    Mar. 6, 2008

Related U.S. Application Data

(62) Division of application No. 11/083,327, filed on Mar. 18, 2005, now Pat. No. 7,288,402.

(30) Foreign Application Priority Data

Mar. 20, 2004   (DE)  ................ 10 2004 013 824

(51) Int. Cl.
*C12P 13/02*   (2006.01)
*C12P 21/06*   (2006.01)
*C12N 9/08*   (2006.01)
*C07H 21/04*   (2006.01)

(52) U.S. Cl. .............. 435/129; 435/228; 435/69.1; 435/252.2; 435/320.1; 435/252.3; 536/23.2

(58) Field of Classification Search ............... None
See application file for complete search history.

(56) References Cited

U.S. PATENT DOCUMENTS

| 5,807,730 A | 9/1998 | Ito et al. ............. 435/232 |
| 2004/0142447 A1 | 7/2004 | Robins et al. ............. 435/227 |

FOREIGN PATENT DOCUMENTS

| DE | 101 55 928 | 11/2001 |
| EP | 0 362 829 | 7/1995 |
| EP | 0 790 310 | 8/1997 |
| EP | 1 055 724 | 11/2000 |
| JP | 5-284982 | 11/1993 |
| WO | WO/98/32872 | 7/1998 |
| WO | WO 01/60789 | 8/2001 |
| WO | WO 02/055670 | 7/2002 |
| WO | WO 02/070717 | 9/2002 |

OTHER PUBLICATIONS

Brady, et al., "Characterisation of Nitrilase and Nitrile Hydratase Biocatalytic Systems," *Appl. Microbiol. Biotechnol.* 64:76-85 (2004).
Ingvorsen, et al., "Microbial Hydrolysis of Organic Nitriles and Amides," *CIBA Foundation Symposium* 140:16-31 (1988).
Lee, "High Cell-Density Culture of *Escherichia coli*," *TIBECH* 14:98-105 (1996).
Kobayashi, et al., "Cobalt Proteins," *Eur. J. Biochem.* 261:1-9 (1999).
Kobayashi, et al., "Enzymatic Synthesis of Acrylamide: A Success Story Not Yet Over," *TIBECH* 10:402-408 (1992).
Komeda, et al., "A Novel Transporter Involved in Cobalt Uptake," *Proc. Natl. Acad. Sci. USA* 94:36-41 (1997).
Martinkova, et al., "Synthetic Applications of Nitrile-Converting Enzymes," *Curr. Org. Chem.* 7:1279-1295 (2003).
Nojiri, et al., "Functional Expression of Nitrile Hydratase in *Escherichia coli*: Requirement of a Nitrile Hydratase Activator and Post-Translational Modification of a Ligand Cysteine," *J. Biochem.* 125:696-704 (1999).
Riesenberg, et al., "High-Cell Density Cultivation of Microorganisms," *Appl. Microbiol. Biotechnol.* 51:422-430 (1999).
Wu, et al., "Over-Production of Stereoselective Nitrile Hydratase from *Pseudomonas putida* 5B in *Escherichia coli*: Activity Requires a Novel Downstream Protein," *App. Microbiol. Biotechnol.* 48:704-708 (1997).
English Language Abstract for Reference B3 above—WO 02/055670.
English Language Abstract for Reference B above—DE 101 55 928.
English Language Abstract for Reference B9 above—JP 5-284982.
Shimizu, et al., Accession No. E 13809 (JP 1997234075, Sep. 9, 1997).

*Primary Examiner*—Rebecca E. Prouty
*Assistant Examiner*—Mohammad Younus Meah
(74) *Attorney, Agent, or Firm*—Michael A. Sanzo; Law Office of Michael A. Sanzo, LLC

(57) ABSTRACT

The invention relates to a *Rhodococcus* polynucleotide cluster which contains nucleotide sequences which encode polypeptides having the activity of a nitrile hydratase, of an auxiliary protein P15K which activates this enzyme and of a cobalt transporter, to transformed microorganisms in which the nucleotide sequences encoding these proteins are present in increased quantity, and to the use of the transformed microorganisms for preparing amides from nitriles.

20 Claims, 3 Drawing Sheets

SEQUENCE LISTING

<160> NUMBER OF SEQ ID NOS: 25

<210> SEQ ID NO 1
<211> LENGTH: 3146
<212> TYPE: DNA
<213> ORGANISM: Rhodococcus opacus
<220> FEATURE:
<221> NAME/KEY: CDS
<222> LOCATION: (1)..(708)
<223> OTHER INFORMATION:
<220> FEATURE:
<221> NAME/KEY: CDS
<222> LOCATION: (710)..(1327)
<223> OTHER INFORMATION:
<220> FEATURE:
<221> NAME/KEY: CDS
<222> LOCATION: (2076)..(3146)
<223> OTHER INFORMATION:

<400> SEQUENCE: 1

```
atg aac ggc atc ttc gat cta ggc gga acc gac ggc atg ggg ccg gtc      48
Met Asn Gly Ile Phe Asp Leu Gly Gly Thr Asp Gly Met Gly Pro Val
1               5                   10                  15 gac aac gac aaa ggc acc gag ccg gtg ttc cgc tca gcg tgg gaa aag      96
Asp Asn Asp Lys Gly Thr Glu Pro Val Phe Arg Ser Ala Trp Glu Lys
            20                  25                  30 gcc gcc ttc tcg atg ttc gca caa ggc gcc cga gct ggc ctc tac aac     144
Ala Ala Phe Ser Met Phe Ala Gln Gly Ala Arg Ala Gly Leu Tyr Asn
        35                  40                  45 atc gac gag ttc cgg cac tgc gtc gag cag atg gac ccc gcc gag tat     192
Ile Asp Glu Phe Arg His Cys Val Glu Gln Met Asp Pro Ala Glu Tyr
50                  55                  60 tta cta tcg aac tac tac gag cac tgg acg cat gcc gtc gaa cac ttc     240
Leu Leu Ser Asn Tyr Tyr Glu His Trp Thr His Ala Val Glu His Phe
65                  70                  75                  80 gcc cag caa aag aac ctc atc aca gcg gca gag ctc gaa aag cgc acg     288
Ala Gln Gln Lys Asn Leu Ile Thr Ala Ala Glu Leu Glu Lys Arg Thr
            85                  90                  95 cat ttc tac cgg gat aac cca gaa gcc ccc ctt ccg gag cgc aag gac     336
His Phe Tyr Arg Asp Asn Pro Glu Ala Pro Leu Pro Glu Arg Lys Asp
        100                 105                 110 cca gag ctc ctc gac ttc gtg aac acc gcg atc gcg aac ggt ttc gcg     384
Pro Glu Leu Leu Asp Phe Val Asn Thr Ala Ile Ala Asn Gly Phe Ala
    115                 120                 125 gcc tcc cgt gaa acc aat agg tcg gca gca ttc acc atc ggc gac cag     432
Ala Ser Arg Glu Thr Asn Arg Ser Ala Ala Phe Thr Ile Gly Asp Gln
130                 135                 140 gta ctg att gct gcg gac agt cca ttc gga cac acc cga cgg gcc ggc     480
Val Leu Ile Ala Ala Asp Ser Pro Phe Gly His Thr Arg Arg Ala Gly
145                 150                 155                 160 tac atc cgc ggt aag acc gga gtc atc acc gcg aca cac ggc gcc tac     528
Tyr Ile Arg Gly Lys Thr Gly Val Ile Thr Ala Thr His Gly Ala Tyr
                165                 170                 175 gtc tat ccc gac acc gcc ggt aac ggg ctc ggt gag tgc cca gag cac     576
Val Tyr Pro Asp Thr Ala Gly Asn Gly Leu Gly Glu Cys Pro Glu His
            180                 185                 190 gtc tac acc gtg aag ttc acc gcc acc gaa ctt tgg ggc gaa cag agc     624
Val Tyr Thr Val Lys Phe Thr Ala Thr Glu Leu Trp Gly Glu Gln Ser
        195                 200                 205 ggt gat cgc cac agc acc gtc tat ttc gat gtc tgg gaa ccg tac ctc     672
Gly Asp Arg His Ser Thr Val Tyr Phe Asp Val Trp Glu Pro Tyr Leu
    210                 215                 220 tcg ctc gct acc gca ccc tct act cga gga atc tga c atg gcc gaa cag  721
Ser Leu Ala Thr Ala Pro Ser Thr Arg Gly Ile        Met Ala Glu Gln
225                 230                 235 cgc acc gac acc caa ttg cgt aca cac gaa gaa gtc gtc gcc cga gtc     769
Arg Thr Asp Thr Gln Leu Arg Thr His Glu Glu Val Val Ala Arg Val
240                 245                 250                 255 aag gcg ctc gag gcg ctg ctg atc gag aaa ggc gtc atg acg acc gag     817
Lys Ala Leu Glu Ala Leu Leu Ile Glu Lys Gly Val Met Thr Thr Glu
            260                 265                 270 gcc gtc gac cgg atg gcc gag gta tac gag aac gaa gtc ggc ccc cag     865
Ala Val Asp Arg Met Ala Glu Val Tyr Glu Asn Glu Val Gly Pro Gln
        275                 280                 285 atc ggc gct cag att gtc gcc aag gcg tgg acc gac ccg aag ttc aag     913
Ile Gly Ala Gln Ile Val Ala Lys Ala Trp Thr Asp Pro Lys Phe Lys
    290                 295                 300 aag agg ttg ctg gcc aat gcc acg act gcc tgc gca gag atg ggc tac     961
Lys Arg Leu Leu Ala Asn Ala Thr Thr Ala Cys Ala Glu Met Gly Tyr
```

-continued

|     |     |     | 305 |     |     |     |     | 310 |     |     |     |     | 315 |     |     |      |
|---|---|---|---|---|---|---|---|---|---|---|---|---|---|---|---|---|
| ggc | ggt | ctg | cag | ggc | gaa | gac | atg | atc | gtc | gtg | gaa | aac | acc | gac | acc | 1009 |
| Gly | Gly | Leu | Gln | Gly | Glu | Asp | Met | Ile | Val | Val | Glu | Asn | Thr | Asp | Thr |      |
| 320 |     |     |     |     | 325 |     |     |     |     | 330 |     |     |     |     | 335 |      |

| gta | cac | aac | gcg | att | gtg | tgc | acc | ctc | tgc | tcc | tgc | tac | ccg | tgg | ccg | 1057 |
|---|---|---|---|---|---|---|---|---|---|---|---|---|---|---|---|---|
| Val | His | Asn | Ala | Ile | Val | Cys | Thr | Leu | Cys | Ser | Cys | Tyr | Pro | Trp | Pro |      |
|     |     |     |     | 340 |     |     |     |     | 345 |     |     |     |     | 350 |     |      |

| gtc | ttg | ggc | ctg | cca | ccg | aac | tgg | tac | aag | gca | ccg | gct | tac | cgc | gca | 1105 |
|---|---|---|---|---|---|---|---|---|---|---|---|---|---|---|---|---|
| Val | Leu | Gly | Leu | Pro | Pro | Asn | Trp | Tyr | Lys | Ala | Pro | Ala | Tyr | Arg | Ala |      |
|     |     |     | 355 |     |     |     |     | 360 |     |     |     |     | 365 |     |     |      |

| cgg | atc | gtg | cgc | gaa | ccg | cgg | aag | gtc | ctc | gcc | gag | gac | ttc | gac | ttt | 1153 |
|---|---|---|---|---|---|---|---|---|---|---|---|---|---|---|---|---|
| Arg | Ile | Val | Arg | Glu | Pro | Arg | Lys | Val | Leu | Ala | Glu | Asp | Phe | Asp | Phe |      |
|     |     | 370 |     |     |     |     | 375 |     |     |     |     | 380 |     |     |     |      |

| ccc | atc | ccc | gac | gac | gtc | gag | atc | cgc | gtg | tgg | gac | tcg | agc | gcc | gag | 1201 |
|---|---|---|---|---|---|---|---|---|---|---|---|---|---|---|---|---|
| Pro | Ile | Pro | Asp | Asp | Val | Glu | Ile | Arg | Val | Trp | Asp | Ser | Ser | Ala | Glu |      |
|     | 385 |     |     |     |     | 390 |     |     |     |     | 395 |     |     |     |     |      |

| ctg | cgc | tat | tgg | gtt | tta | ccg | cag | cgc | cct | gca | cac | acc | gaa | aga | ttg | 1249 |
|---|---|---|---|---|---|---|---|---|---|---|---|---|---|---|---|---|
| Leu | Arg | Tyr | Trp | Val | Leu | Pro | Gln | Arg | Pro | Ala | His | Thr | Glu | Arg | Leu |      |
| 400 |     |     |     |     | 405 |     |     |     |     | 410 |     |     |     |     | 415 |      |

| acg | gaa | tcc | gag | ctg | gta | gcg | ctg | gtc | acc | cgc | gac | tcg | atg | atc | ggt | 1297 |
|---|---|---|---|---|---|---|---|---|---|---|---|---|---|---|---|---|
| Thr | Glu | Ser | Glu | Leu | Val | Ala | Leu | Val | Thr | Arg | Asp | Ser | Met | Ile | Gly |      |
|     |     |     |     | 420 |     |     |     |     | 425 |     |     |     |     | 430 |     |      |

| gtg | gga | ccg | gtg | agg | gag | gcg | atg | tcg | tga | gcacgcgcat tgacgcaacc | 1347 |
|---|---|---|---|---|---|---|---|---|---|---|---|
| Val | Gly | Pro | Val | Arg | Glu | Ala | Met | Ser |     |     |      |
|     |     |     | 435 |     |     |     |     | 440 |     |     |      |

```
gagctcgggg aagcacgccg gcgaatcgag gcgttggtgt gtgatctgcc cggtggtgac   1407
gtaggctcac gcgccttcaa cgagccgtgg gaattgcgtg ccttcgcgat ggccgttgcc   1467
gtgtatcacc agggtcacta cgaatggagt gagtttcagc tctccctgat cgcgtcgatc   1527
cgccactggg agcagggcga gggaagggag ccgtggagct actacgagca ctggctcaat   1587
gcgctcgagt cggtactcgc cgccagcggc gccttatcgg acgcagtggg cctcgatgag   1647
cgcacgcgcg aagttctcac caccccacgg aacacgaacc accaccatgc acatcgcgaa   1707
cccgtcgcga tctcatctgc ggtgaactaa cccgcggcgc tactcgtccg ctggccagct   1767
ctctgcctgc tgtccagcga acgacacctc cgtgacagct tctcgttcac cgacccgatc   1827
actgattccc gacgcggtta ccaacgagca cccgcgtata aacagaaccg caaaggtatc   1887
gcagctgtcg gggacgagcg aatagcggat cgctcgcggg ggccggaccc atgcagctga   1947
tgctgctttc gcccgaatag cccagatatc cactggacga ggtgcgaggc ccgatacaag   2007
gcgagcgtca gcaaccggca aaccacagcg tccagagcca gcaccgtcat gtctagaaga   2067
```

| ggaaagca  | ttg | acg | att | act | acc | act | tcg | cca | agg | cag | atc | gcc | ggt | cgg | 2117 |
|---|---|---|---|---|---|---|---|---|---|---|---|---|---|---|---|
|           | Leu | Thr | Ile | Thr | Thr | Thr | Ser | Pro | Arg | Gln | Ile | Ala | Gly | Arg |      |
|           |     |     |     |     | 445 |     |     |     |     | 450 |     |     |     |     |      |

| tgg | aca | cgt | gcc | gag | cgg | caa | cga | ctg | agc | gct | atc | atc | ggc | acc | atc | 2165 |
|---|---|---|---|---|---|---|---|---|---|---|---|---|---|---|---|---|
| Trp | Thr | Arg | Ala | Glu | Arg | Gln | Arg | Leu | Ser | Ala | Ile | Ile | Gly | Thr | Ile |      |
| 455 |     |     |     |     | 460 |     |     |     |     | 465 |     |     |     |     | 470 |      |

| gca | ttg | ctg | cac | gtg | cta | ggt | atc | gca | atg | tat | ctc | ggg | cgc | tcg | ggt | 2213 |
|---|---|---|---|---|---|---|---|---|---|---|---|---|---|---|---|---|
| Ala | Leu | Leu | His | Val | Leu | Gly | Ile | Ala | Met | Tyr | Leu | Gly | Arg | Ser | Gly |      |
|     |     |     |     | 475 |     |     |     |     | 480 |     |     |     |     | 485 |     |      |

| aac | ccg | gcc | gcc | gct | ggt | agc | ctg | gct | ggc | tcg | gga | ctg | ctc | gcc | tat | 2261 |
|---|---|---|---|---|---|---|---|---|---|---|---|---|---|---|---|---|
| Asn | Pro | Ala | Ala | Ala | Gly | Ser | Leu | Ala | Gly | Ser | Gly | Leu | Leu | Ala | Tyr |      |
|     |     |     | 490 |     |     |     |     | 495 |     |     |     |     | 500 |     |     |      |

| gtc | ctg | ggt | gcg | cgg | cac | gcg | ttc | gat | gcc | gac | cac | atc | gcg | gcc | atc | 2309 |
|---|---|---|---|---|---|---|---|---|---|---|---|---|---|---|---|---|
| Val | Leu | Gly | Ala | Arg | His | Ala | Phe | Asp | Ala | Asp | His | Ile | Ala | Ala | Ile |      |
|     |     |     |     | 505 |     |     |     |     | 510 |     |     |     |     | 515 |     |      |

| gac | gac | acc | acc | cgc | atc | atg | ctc | ctt | cgc | gga | cgc | cga | ccc | gtc | ggc | 2357 |
|---|---|---|---|---|---|---|---|---|---|---|---|---|---|---|---|---|

-continued

```
            Asp Asp Thr Thr Arg Ile Met Leu Leu Arg Gly Arg Arg Pro Val Gly
                520                 525                 530 gtc gga ttc ttt ttc gcc atg ggg cat tcg act gtc gtc ctc gtt ctc        2405
Val Gly Phe Phe Phe Ala Met Gly His Ser Thr Val Val Leu Val Leu
535                 540                 545                 550 tct ctg atc gtc gct ttc gga gcg ggc tcg ctc agt tcg atg gaa gcg        2453
Ser Leu Ile Val Ala Phe Gly Ala Gly Ser Leu Ser Ser Met Glu Ala
                555                 560                 565 tcc cgg gtc gag gag atc gga ggt tac gtc gcg acc tgc gtg gca gtg        2501
Ser Arg Val Glu Glu Ile Gly Gly Tyr Val Ala Thr Cys Val Ala Val
            570                 575                 580 ctg ttc ttg gtg ctg gtg gcc gca ctc aac agt ttc gtt ctg cgc aag        2549
Leu Phe Leu Val Leu Val Ala Ala Leu Asn Ser Phe Val Leu Arg Lys
        585                 590                 595 ctc ctc gct ctg tct cgt cgg atg cgc act ggg gaa gat atc tcc ggc        2597
Leu Leu Ala Leu Ser Arg Arg Met Arg Thr Gly Glu Asp Ile Ser Gly
    600                 605                 610 gac ctc gag cgc ggg ctg ggt gaa cgg gga ttg ctc agc tgg ctt ctc        2645
Asp Leu Glu Arg Gly Leu Gly Glu Arg Gly Leu Leu Ser Trp Leu Leu
615                 620                 625                 630 agc ggc cga ttg cgc ggg ctg att cgt tcg tcc tgg cac atg tac ccg        2693
Ser Gly Arg Leu Arg Gly Leu Ile Arg Ser Ser Trp His Met Tyr Pro
                635                 640                 645 gtg ggc ctg ctc atg ggt ctc ggc ctg gaa acc gca tcc gaa gtg aca        2741
Val Gly Leu Leu Met Gly Leu Gly Leu Glu Thr Ala Ser Glu Val Thr
            650                 655                 660 ttg ctg tct ctc act gcc tcc gca gcg agc gga ggt cag cta tcg cta        2789
Leu Leu Ser Leu Thr Ala Ser Ala Ala Ser Gly Gly Gln Leu Ser Leu
        665                 670                 675 atg gcg att gtg agc ctt cca ttg ttg ttt gcc gcg ggg atg agc acc        2837
Met Ala Ile Val Ser Leu Pro Leu Leu Phe Ala Ala Gly Met Ser Thr
    680                 685                 690 ttc gat act gca gac tca ctc gtc atg acc cgc gcc tat tcg tgg tcc        2885
Phe Asp Thr Ala Asp Ser Leu Val Met Thr Arg Ala Tyr Ser Trp Ser
695                 700                 705                 710 tat aac gat gcc cag cgc cgc ctt cgc ttc aac act gta acc acg ggt        2933
Tyr Asn Asp Ala Gln Arg Arg Leu Arg Phe Asn Thr Val Thr Thr Gly
                715                 720                 725 gcg acc atg gtc atc ggg ttc ttc gtc gcg gga atc tac gtt tct gga        2981
Ala Thr Met Val Ile Gly Phe Phe Val Ala Gly Ile Tyr Val Ser Gly
            730                 735                 740 ctg ctt gcg ccg cta cca ggg ttc ggt tgg ctg acc cct ctg ggc gcg        3029
Leu Leu Ala Pro Leu Pro Gly Phe Gly Trp Leu Thr Pro Leu Gly Ala
        745                 750                 755 atc gcc gac aac ttc gag ttc ctc ggc tac gca gtc gcc gga ttg ttc        3077
Ile Ala Asp Asn Phe Glu Phe Leu Gly Tyr Ala Val Ala Gly Leu Phe
    760                 765                 770 gtt gct acc tgg gca atc gca gca ctg gtt agc cgg cct cga cgg ctt        3125
Val Ala Thr Trp Ala Ile Ala Ala Leu Val Ser Arg Pro Arg Arg Leu
775                 780                 785                 790 gtc ggc agc tcg aag gtg tga                                            3146
Val Gly Ser Ser Lys Val
                795
```

<210> SEQ ID NO 2
<211> LENGTH: 235
<212> TYPE: PRT
<213> ORGANISM: Rhodococcus opacus

<400> SEQUENCE: 2

```
Met Asn Gly Ile Phe Asp Leu Gly Gly Thr Asp Gly Met Gly Pro Val
1               5                   10                  15

Asp Asn Asp Lys Gly Thr Glu Pro Val Phe Arg Ser Ala Trp Glu Lys
                20                  25                  30

Ala Ala Phe Ser Met Phe Ala Gln Gly Ala Arg Ala Gly Leu Tyr Asn
            35                  40                  45

Ile Asp Glu Phe Arg His Cys Val Glu Gln Met Asp Pro Ala Glu Tyr
50                  55                  60

Leu Leu Ser Asn Tyr Tyr Glu His Trp Thr His Ala Val Glu His Phe
65              70                  75                  80

Ala Gln Gln Lys Asn Leu Ile Thr Ala Ala Glu Leu Glu Lys Arg Thr
                85                  90                  95

His Phe Tyr Arg Asp Asn Pro Glu Ala Pro Leu Pro Gly Arg Lys Asp
                100                 105                 110

Pro Glu Leu Leu Asp Phe Val Asn Thr Ala Ile Ala Asn Gly Phe Ala
            115                 120                 125

Ala Ser Arg Glu Thr Asn Arg Ser Ala Ala Phe Thr Ile Gly Asp Gln
130                 135                 140

Val Leu Ile Ala Ala Asp Ser Pro Phe Gly His Thr Arg Arg Ala Gly
145                 150                 155                 160

Tyr Ile Arg Gly Lys Thr Gly Val Ile Thr Ala Thr His Gly Ala Tyr
                165                 170                 175

Val Tyr Pro Asp Thr Ala Gly Asn Gly Leu Gly Glu Cys Pro Glu His
            180                 185                 190

Val Tyr Thr Val Lys Phe Thr Ala Thr Glu Leu Trp Gly Glu Gln Ser
            195                 200                 205

Gly Asp Arg His Ser Thr Val Tyr Phe Asp Val Trp Glu Pro Tyr Leu
            210                 215                 220

Ser Leu Ala Thr Ala Pro Ser Thr Arg Gly Ile
225                 230                 235

<210> SEQ ID NO 3
<211> LENGTH: 205
<212> TYPE: PRT
<213> ORGANISM: Rhodococcus opacus

<400> SEQUENCE: 3

Met Ala Glu Gln Arg Thr Asp Thr Gln Leu Arg Thr His Glu Glu Val
1               5                   10                  15

Val Ala Arg Val Lys Ala Leu Glu Ala Leu Leu Ile Glu Lys Gly Val
                20                  25                  30

Met Thr Thr Glu Ala Val Asp Arg Met Ala Glu Val Tyr Glu Asn Glu
            35                  40                  45

Val Gly Pro Gln Ile Gly Ala Gln Ile Val Ala Lys Ala Trp Thr Asp
50                  55                  60

Pro Lys Phe Lys Lys Arg Leu Leu Ala Asn Ala Thr Thr Ala Cys Ala
65                  70                  75                  80

Glu Met Gly Tyr Gly Gly Leu Gln Gly Glu Asp Met Ile Val Val Glu
                85                  90                  95

Asn Thr Asp Thr Val His Asn Ala Ile Val Cys Thr Leu Cys Ser Cys
                100                 105                 110

Tyr Pro Trp Pro Val Leu Gly Leu Pro Pro Asn Trp Tyr Lys Ala Pro
            115                 120                 125

Ala Tyr Arg Ala Arg Ile Val Arg Glu Pro Arg Lys Val Leu Ala Glu
130                 135                 140
```

```
Asp Phe Asp Phe Pro Ile Pro Asp Asp Val Glu Ile Arg Val Trp Asp
145                 150                 155                 160

Ser Ser Ala Glu Leu Arg Tyr Trp Val Leu Pro Gln Arg Pro Ala His
            165                 170                 175

Thr Glu Arg Leu Thr Glu Ser Glu Leu Val Ala Leu Val Thr Arg Asp
            180                 185                 190

Ser Met Ile Gly Val Gly Pro Val Arg Glu Ala Met Ser
            195                 200                 205

<210> SEQ ID NO 4
<211> LENGTH: 356
<212> TYPE: PRT
<213> ORGANISM: Rhodococcus opacus

<400> SEQUENCE: 4

Leu Thr Ile Thr Thr Thr Ser Pro Arg Gln Ile Ala Gly Arg Trp Thr
1               5                   10                  15

Arg Ala Glu Arg Gln Arg Leu Ser Ala Ile Ile Gly Thr Ile Ala Leu
            20                  25                  30

Leu His Val Leu Gly Ile Ala Met Tyr Leu Gly Arg Ser Gly Asn Pro
            35                  40                  45

Ala Ala Ala Gly Ser Leu Ala Gly Ser Gly Leu Leu Ala Tyr Val Leu
    50                  55                  60

Gly Ala Arg His Ala Phe Asp Ala Asp His Ile Ala Ala Ile Asp Asp
65                  70                  75                  80

Thr Thr Arg Ile Met Leu Leu Arg Gly Arg Arg Pro Val Gly Val Gly
                85                  90                  95

Phe Phe Phe Ala Met Gly His Ser Thr Val Val Leu Val Leu Ser Leu
            100                 105                 110

Ile Val Ala Phe Gly Ala Gly Ser Leu Ser Ser Met Glu Ala Ser Arg
            115                 120                 125

Val Glu Glu Ile Gly Gly Tyr Val Ala Thr Cys Val Ala Val Leu Phe
130                 135                 140

Leu Val Leu Val Ala Ala Leu Asn Ser Phe Val Leu Arg Lys Leu Leu
145                 150                 155                 160

Ala Leu Ser Arg Arg Met Arg Thr Gly Glu Asp Ile Ser Gly Asp Leu
            165                 170                 175

Glu Arg Gly Leu Gly Glu Arg Gly Leu Leu Ser Trp Leu Leu Ser Gly
            180                 185                 190

Arg Leu Arg Gly Leu Ile Arg Ser Ser Trp His Met Tyr Pro Val Gly
            195                 200                 205

Leu Leu Met Gly Leu Gly Leu Glu Thr Ala Ser Glu Val Thr Leu Leu
            210                 215                 220

Ser Leu Thr Ala Ser Ala Ala Ser Gly Gly Gln Leu Ser Leu Met Ala
225                 230                 235                 240

Ile Val Ser Leu Pro Leu Leu Phe Ala Ala Gly Met Ser Thr Phe Asp
            245                 250                 255

Thr Ala Asp Ser Leu Val Met Thr Arg Ala Tyr Ser Trp Ser Tyr Asn
            260                 265                 270

Asp Ala Gln Arg Arg Leu Arg Phe Asn Thr Val Thr Thr Gly Ala Thr
            275                 280                 285

Met Val Ile Gly Phe Phe Val Ala Gly Ile Tyr Val Ser Gly Leu Leu
            290                 295                 300

Ala Pro Leu Pro Gly Phe Gly Trp Leu Thr Pro Leu Gly Ala Ile Ala
```

```
                305                 310                 315                 320
Asp Asn Phe Glu Phe Leu Gly Tyr Ala Val Ala Gly Leu Phe Val Ala
                325                 330                 335
Thr Trp Ala Ile Ala Ala Leu Val Ser Arg Pro Arg Leu Val Gly
                340                 345                 350
Ser Ser Lys Val
        355

<210> SEQ ID NO 5
<211> LENGTH: 3146
<212> TYPE: DNA
<213> ORGANISM: Rhodococcus opacus
<220> FEATURE:
<221> NAME/KEY: CDS
<222> LOCATION: (1324)..(1737)
<223> OTHER INFORMATION:

<400> SEQUENCE: 5
atgaacggca tcttcgatct aggcggaacc gacggcatgg ggccggtcga caacgacaaa         60
ggcaccgagc cggtgttccg ctcagcgtgg gaaaaggccg ccttctcgat gttcgcacaa        120
ggcgcccgag ctggcctcta caacatcgac gagttccggc actgcgtcga gcagatggac        180
cccgccgagt atttactatc gaactactac gagcactgga cgcatgccgt cgaacacttc        240
gcccagcaaa agaacctcat cacagcggca gagctcgaaa agcgcacgca tttctaccgg        300
gataacccag aagcccccct tccggagcgc aaggacccag agctcctcga cttcgtgaac        360
accgcgatcg cgaacggttt cgcggcctcc cgtgaaacca ataggtcggc agcattcacc        420
atcggcgacc aggtactgat tgctgcggac agtccattcg acacacccg acgggccggc        480 tacatccgcg gtaagaccgg agtcatcacc gcgacacacg cgcctacgt ctatcccgac        540 accgccggta acgggctcgg tgagtgccca gagcacgtct acaccgtgaa gttcaccgcc        600
accgaacttt ggggcgaaca gagcggtgat cgccacagca ccgtctattt cgatgtctgg        660
gaaccgtacc tctcgctcgc taccgcaccc tctactcgag aatctgaca tggccgaaca        720 gcgcaccgac acccaattgc gtacacacga agaagtcgtc gcccgagtca aggcgctcga        780
ggcgctgctg atcgagaaag gcgtcatgac gaccgaggcc gtcgaccgga tggccgaggt        840
atacgagaac gaagtcggcc ccagatcgg cgctcagatt gtcgccaagg cgtgaccga         900 cccgaagttc aagaagaggt tgctggccaa tgccacgact gcctgcgcag agatgggcta        960
cggcggtctg cagggcgaag acatgatcgt cgtggaaaac accgacaccg tacacaacgc       1020
gattgtgtgc accctctgct cctgctaccc gtggccggtc ttgggcctgc accgaactg        1080 gtacaaggca ccggcttacc gcgcacggat cgtgcgcgaa ccgcggaagg tcctcgccga       1140
ggacttcgac tttcccatcc ccgacgacgt cgagatccgc gtgtgggact cgagcgccga       1200
gctgcgctat tgggttttac cgcagcgccc tgcacacacc gaaagattga cggaatccga       1260
gctggtagcg ctggtcaccc cgactcgat gatcggtgtg ggaccggtga gggaggcgat       1320 gtc gtg agc acg cgc att gac gca acc gag ctc ggg gaa gca cgc cgg       1368
Val Ser Thr Arg Ile Asp Ala Thr Glu Leu Gly Glu Ala Arg Arg
  1               5                  10                  15 cga atc gag gcg ttg gtg tgt gat ctg ccc ggt ggt gac gta ggc tca       1416
Arg Ile Glu Ala Leu Val Cys Asp Leu Pro Gly Gly Asp Val Gly Ser
            20                  25                  30 cgc gcc ttc aac gag ccg tgg gaa ttg cgt gcc ttc gcg atg gcc gtt       1464
Arg Ala Phe Asn Glu Pro Trp Glu Leu Arg Ala Phe Ala Met Ala Val
        35                  40                  45
```

```
gcc gtg tat cac cag ggt cac tac gaa tgg agt gag ttt cag ctc tcc      1512
Ala Val Tyr His Gln Gly His Tyr Glu Trp Ser Glu Phe Gln Leu Ser
         50                  55                  60 ctg atc gcg tcg atc cgc cac tgg gag cag ggc gag gga agg gag ccg      1560
Leu Ile Ala Ser Ile Arg His Trp Glu Gln Gly Glu Gly Arg Glu Pro
 65                  70                  75 tgg agc tac tac gag cac tgg ctc aat gcg ctc gag tcg gta ctc gcc      1608
Trp Ser Tyr Tyr Glu His Trp Leu Asn Ala Leu Glu Ser Val Leu Ala
 80                  85                  90                  95 gcc agc ggc gcc tta tcg gac gca gtg ggc ctc gat gag cgc acg cgc      1656
Ala Ser Gly Ala Leu Ser Asp Ala Val Gly Leu Asp Glu Arg Thr Arg
                100                 105                 110 gaa gtt ctc acc acc cca cgg aac acg aac cac cac cat gca cat cgc      1704
Glu Val Leu Thr Thr Pro Arg Asn Thr Asn His His His Ala His Arg
            115                 120                 125 gaa ccc gtc gcg atc tca tct gcg gtg aac taa cccgcggcgc tactcgtccg   1757
Glu Pro Val Ala Ile Ser Ser Ala Val Asn
        130                 135 ctggccagct ctctgcctgc tgtccagcga acgacacctc cgtgacagct tctcgttcac    1817 cgaccccgatc actgattccc gacgcggtta ccaacgagca cccgcgtata aacagaaccg   1877
caaaggtatc gcagctgtcg gggacgagcg aatagcggat cgctcgcggg ggccggaccc    1937
atgcagctga tgctgctttc gcccgaatag cccagatatc cactgaacga ggtgcgaggc    1997
ccgatacaag gcgagcgtca gcaaccggca aaccacagcg tccagagcca gcaccgtcat    2057
gtctagaaga ggaaagcatt gacgattact accacttcgc caaggcagat cgccggtcgg    2117
tggacacgtg ccgagcggca acgactgagc gctatcatcg gcaccatcgc attgctgcac    2177
gtgctaggta tcgcaatgta tctcgggcgc tcgggtaacc cggccgccgc tggtagcctg    2237
gctggctcgg gactgctcgc ctatgtcctg ggtgcgcggc acgcgttcga tgccgaccac    2297
atcgcggcca tcgacgacac cacccgcatc atgctccttc gcggacgccg acccgtcggc    2357
gtcggattct ttttcgccat ggggcattcg actgtcgtcc tcgttctctc tctgatcgtc    2417
gctttcggag cgggctcgct cagttcgatg gaagcgtccc gggtcgagga gatcggaggt    2477
tacgtcgcga cctgcgtggc agtgctgttc ttggtgctgg tggccgcact caacagtttc    2537
gttctgcgca agctcctcgc tctgtctcgt cggatgcgca ctggggaaga tatctccggc    2597
gacctcgagc gcgggctggg tgaacgggga ttgctcagct ggcttctcag cggccgattg    2657
cgcgggctga ttcgttcgtc ctggcacatg tacccggtgg gcctgctcat gggtctcggc    2717
ctggaaaccg catccgaagt gacattgctg tctctcactg cctccgcagc gagcggaggt    2777
cagctatcgc taatggcgat tgtgagcctt ccattgttgt ttgccgcggg gatgagcacc    2837
ttcgatactg cagactcact cgtcatgacc cgcgcctatt cgtggtccta taacgatgcc    2897
cagcgccgcc ttcgcttcaa cactgtaacc acgggtgcga ccatggtcat cgggttcttc    2957
gtcgcgggaa tctacgtttc tggactgctt gcgccgctac cagggttcgg ttggctgacc    3017
cctctgggcg cgatcgccga caacttcgag ttcctcggct acgcagtcgc cggattgttc    3077
gttgctacct gggcaatcgc agcactggtt agccggcctc gacggcttgt cggcagctcg    3137
aaggtgtga                                                            3146
```

<210> SEQ ID NO 6
<211> LENGTH: 137
<212> TYPE: PRT
<213> ORGANISM: Rhodococcus opacus

<400> SEQUENCE: 6

```
Val Ser Thr Arg Ile Asp Ala Thr Glu Leu Gly Glu Ala Arg Arg
1               5                  10                  15

Ile Glu Ala Leu Val Cys Asp Leu Pro Gly Gly Asp Val Gly Ser Arg
                20                  25                  30

Ala Phe Asn Glu Pro Trp Glu Leu Arg Ala Phe Ala Met Ala Val Ala
            35                  40                  45

Val Tyr His Gln Gly His Tyr Glu Trp Ser Glu Phe Gln Leu Ser Leu
        50                  55                  60

Ile Ala Ser Ile Arg His Trp Glu Gln Gly Glu Gly Arg Glu Pro Trp
65                  70                  75                  80

Ser Tyr Tyr Glu His Trp Leu Asn Ala Leu Glu Ser Val Leu Ala Ala
                85                  90                  95

Ser Gly Ala Leu Ser Asp Ala Val Gly Leu Asp Glu Arg Thr Arg Glu
            100                 105                 110

Val Leu Thr Thr Pro Arg Asn Thr Asn His His His Ala His Arg Glu
        115                 120                 125

Pro Val Ala Ile Ser Ser Ala Val Asn
    130             135
```

<210> SEQ ID NO 7
<211> LENGTH: 17
<212> TYPE: DNA
<213> ORGANISM: Artificial
<220> FEATURE:
<223> OTHER INFORMATION: Primer

<400> SEQUENCE: 7
atgaayggha tyttcga                                              17

<210> SEQ ID NO 8
<211> LENGTH: 17
<212> TYPE: DNA
<213> ORGANISM: Artificial
<220> FEATURE:
<223> OTHER INFORMATION: Primer

<400> SEQUENCE: 8
atccagtgyy hgtagta                                              17

<210> SEQ ID NO 9
<211> LENGTH: 19
<212> TYPE: DNA
<213> ORGANISM: Artificial
<220> FEATURE:
<223> OTHER INFORMATION: Primer

<400> SEQUENCE: 9
cgaagacatg atcgtcgtg                                            19

<210> SEQ ID NO 10
<211> LENGTH: 16
<212> TYPE: DNA
<213> ORGANISM: Artificial
<220> FEATURE:
<223> OTHER INFORMATION: Primer

<400> SEQUENCE: 10
accggtccca caccga                                               16

<210> SEQ ID NO 11
<211> LENGTH: 16

```
<212> TYPE: DNA
<213> ORGANISM: Artificial
<220> FEATURE:
<223> OTHER INFORMATION: Primer

<400> SEQUENCE: 11
tcgaggagat cggagg                                                    16

<210> SEQ ID NO 12
<211> LENGTH: 18
<212> TYPE: DNA
<213> ORGANISM: Artificial
<220> FEATURE:
<223> OTHER INFORMATION: Primer

<400> SEQUENCE: 12
gtatcgaagg tgctcatc                                                  18

<210> SEQ ID NO 13
<211> LENGTH: 15
<212> TYPE: DNA
<213> ORGANISM: Artificial
<220> FEATURE:
<223> OTHER INFORMATION: Primer

<400> SEQUENCE: 13
cgcgggctgg gtgaa                                                     15

<210> SEQ ID NO 14
<211> LENGTH: 36
<212> TYPE: DNA
<213> ORGANISM: Artificial
<220> FEATURE:
<223> OTHER INFORMATION: Primer

<400> SEQUENCE: 14
cggcggaatt caagaaggag acccgcatat gaacgg                              36

<210> SEQ ID NO 15
<211> LENGTH: 36
<212> TYPE: DNA
<213> ORGANISM: Artificial
<220> FEATURE:
<223> OTHER INFORMATION: Primer

<400> SEQUENCE: 15
ggtgcaagct tggatcctgt cagattcctc gagtag                              36

<210> SEQ ID NO 16
<211> LENGTH: 33
<212> TYPE: DNA
<213> ORGANISM: Artificial
<220> FEATURE:
<223> OTHER INFORMATION: Primer

<400> SEQUENCE: 16
gcgaaggatc ctgcatgcat cgaaattaat acg                                 33

<210> SEQ ID NO 17
<211> LENGTH: 33
<212> TYPE: DNA
<213> ORGANISM: Artificial
<220> FEATURE:
<223> OTHER INFORMATION: Primer

<400> SEQUENCE: 17
```

```
catcaagctt ttcgccatgg ctatatctcc ttc                                    33
```

<210> SEQ ID NO 18
<211> LENGTH: 37
<212> TYPE: DNA
<213> ORGANISM: Artificial
<220> FEATURE:
<223> OTHER INFORMATION: Primer

<400> SEQUENCE: 18

```
ctgacaggat ccaagaagga gatatagcca tggccga                                37
```

<210> SEQ ID NO 19
<211> LENGTH: 37
<212> TYPE: DNA
<213> ORGANISM: Artificial
<220> FEATURE:
<223> OTHER INFORMATION: Primer

<400> SEQUENCE: 19

```
gttgcaagct tggtaccgct caagacatcg cctccct                                37
```

<210> SEQ ID NO 20
<211> LENGTH: 36
<212> TYPE: DNA
<213> ORGANISM: Artificial
<220> FEATURE:
<223> OTHER INFORMATION: Primer

<400> SEQUENCE: 20

```
gtgggtacca agaaggaggc gatcatatga gcacgc                                 36
```

<210> SEQ ID NO 21
<211> LENGTH: 32
<212> TYPE: DNA
<213> ORGANISM: Artificial
<220> FEATURE:
<223> OTHER INFORMATION: Primer

<400> SEQUENCE: 21

```
gcggacgagt agcgaagctt gttagttcac cg                                     32
```

<210> SEQ ID NO 22
<211> LENGTH: 36
<212> TYPE: DNA
<213> ORGANISM: Artificial
<220> FEATURE:
<223> OTHER INFORMATION: Primer

<400> SEQUENCE: 22

```
tcaaagcttg aaggagatat acatatgacg attact                                 36
```

<210> SEQ ID NO 23
<211> LENGTH: 33
<212> TYPE: DNA
<213> ORGANISM: Artificial
<220> FEATURE:
<223> OTHER INFORMATION: Primer

<400> SEQUENCE: 23

```
gtcaagcttg gtaccgacat ctcacacctt cga                                    33
```

<210> SEQ ID NO 24
<211> LENGTH: 6307
<212> TYPE: DNA
<213> ORGANISM: E. coli, Rhodococcus opacus

<400> SEQUENCE: 24

```
aattcttaag aaggagatat acatatgaac ggcatcttcg atctaggcgg aaccgacggc      60
atggggccgg tcgacaacga caaaggcacc gagccggtgt tccgctcagc gtgggaaaag     120
gccgccttct cgatgttcgc acaaggcgcc cgagctggcc tctacaacat cgacgagttc     180
cggcactgcg tcgagcagat ggaccccgcc gagtatttac tatcgaacta ctacgagcac     240
tggacgcatg ccgtcgaaca cttcgcccag caaaagaacc tcatcacagc ggcagagctc     300
gaaaagcgca cgcatttcta ccgggataac ccagaagccc ccctctccgga gcgcaaggac     360
ccagagctcc tcgacttcgt gaacaccgcg atcgcgaacg gtttcgcggc ctcccgtgaa     420
accaataggt cggcagcatt caccatcggc gaccaggtac tgattgctgc ggacagtcca     480
ttcggacaca cccgacgggc cggctacatc cgcggtaaga ccggagtcat caccgcgaca     540
cacggcgcct acgtctatcc cgacaccgcc ggtaacgggc tcggtgagtg cccagagcac     600
gtctacaccg tgaagttcac cgccaccgaa ctttggggcg aacagagcgg tgatcgccac     660
agcaccgtct atttcgatgt ctgggaaccg tacctctcgc tcgctaccgc accctctact     720
cgaggaatct gacaggatcc tgcatgcatc gaaattaata cgacgaaatt aatacgactc     780
actatagggc aattgcgatc accacaattc agcaaattgt gaacatcatc acgttcatct     840
ttccctggtt gccaatggcc cattttcctg tcagtaacga aaggtcgcg aattcaggcg     900
cttttagac tggtcgtaat gaacaattct taagaaggag atatagccat ggccaacag     960
cgcaccgaca cccaattgcg tacacacgaa gaagtcgtcg cccgagtcaa ggcgctcgag    1020
gcgctgctga tcgagaaagg cgtcatgacg accgaggccg tcgaccggat ggccgaggta    1080
tacgagaacg aagtcggccc ccagatcggc gctcagattg tcgccaaggc gtggaccgac    1140
ccgaagttca agaagaggtt gctggccaat gccacgactg cctgcgcaga gatgggctac    1200
ggcggtctgc agggcgaaga catgatcgtc gtggaaaaca ccgacaccgt acacaacgcg    1260
attgtgtgca ccctctgctc ctgctacccg tggccggtct tgggcctgcc accgaactgg    1320
tacaaggcac cggcttaccg cgcacggatc gtgcgcgaac gcggaaggt cctcgccgag    1380
gacttcgact ttcccatccc cgacgacgtc gagatccgcg tgtgggactc gagcgccgag    1440
ctgcgctatt gggttttacc gcagcgcccc gcacacaccg aaagattgac ggaatccgag    1500
ctggtagcgc tggtcacccg cgactcgatg atcggtgtgg accggtgag ggaggcgatg    1560
tcttgagcgg taccaagaag gaggcgatca tatgagcacg cgcattgacg caaccgagct    1620
cggggaagca cgccggcgaa tcgaggcgtt ggtgtgtgat ctgcccggtg gtgacgtagg    1680
ctcacgcgcc ttcaacgagc cgtgggaatt gcgtgccttc gcgatggccg ttgccgtgta    1740
tcaccagggt cactacgaat ggagtgagtt tcagctctcc ctgatcgcgt cgatccgcca    1800
ctgggagcag ggcgagggaa gggagccgtg gagctactac gagcactggc tcaatgcgct    1860
cgagtcggta ctcgccgcca gcggcgcctt atcggacgca gtgggcctcg atgagcgcac    1920
gcgcgaagtt ctcaccaccc cacggaacac gaaccaccac catgcacatc gcgaacccgt    1980
cgcgatctca tctgcggtga actaacaagc ttggctgttt tggcggatga gagaagattt    2040
tcagcctgat acagattaaa tcagaacgca gaagcggtct gataaaacag aatttgcctg    2100
gcggcagtag cgcggtggtc ccacctgacc ccatgccgaa ctcagaagtg aaacgccgta    2160
gcgccgatgg tagtgtgggg tctccccatg cgagagtagg gaactgccag gcatcaaata    2220
aaacgaaagg ctcagtcgaa agactgggcc tttcgtttta tctgttgttt gtcggtgaac    2280
```

```
gctctcctga gtaggacaaa tccgccggga gcggatttga acgttgcgaa gcaacggccc    2340
ggagggtggc gggcaggacg cccgccataa actgccaggc atcaaattaa gcagaaggcc    2400
atcctgacgg atggccttt tgcgtttcta caaactcttt tgtttatttt tctaaataca    2460
ttcaaatatg tatccgctca tgagacaata accctgataa atgcttcaat aatattgaaa    2520
aaggaagagt atgagtattc aacatttccg tgtcgccctt attcccttt ttgcggcatt    2580 ttgccttcct gtttttgctc acccagaaac gctggtgaaa gtaaagatg ctgaagatca    2640 gttgggtgca cgagtgggtt acatcgaact ggatctcaac agcggtaaga tccttgagag    2700
ttttcgcccc gaagaacgtt ttccaatgat gagcactttt aaagttctgc tatgtggcgc    2760
ggtattatcc cgtgttgacg ccgggcaaga gcaactcggt cgccgcatac actattctca    2820
gaatgacttg gttgagtact caccagtcac agaaaagcat cttacggatg gcatgacagt    2880
aagagaatta tgcagtgctg ccataaccat gagtgataac actgcggcca acttacttct    2940
gacaacgatc ggaggaccga aggagctaac cgcttttttg cacaacatgg ggatcatgt    3000 aactcgcctt gatcgttggg aaccggagct gaatgaagcc ataccaaacg acgagcgtga    3060
caccacgatg cctgtagcaa tggcaacaac gttgcgcaaa ctattaactg gcgaactact    3120
tactctagct tcccggcaac aattaataga ctggatggag gcggataaag ttgcaggacc    3180
acttctgcgc tcggcccttc cggctggctg gtttattgct gataaatctg gagccggtga    3240
gcgtgggtct cgcggtatca ttgcagcact ggggccagat ggtaagccct cccgtatcgt    3300
agttatctac acgacgggga gtcaggcaac tatggatgaa cgaaatagac agatcgctga    3360
gataggtgcc tcactgatta agcattggta actgtcagac caagtttact catatatact    3420
ttagattgat ttaaaacttc attttttaatt taaaaggatc taggtgaaga tcctttttga    3480
taatctcatg accaaaatcc cttaacgtga gttttcgttc cactgagcgt cagaccccgt    3540
agaaaagatc aaaggatctt cttgagatcc tttttttctg cgcgtaatct gctgcttgca    3600
aacaaaaaaa ccaccgctac cagcggtggt ttgtttgccg gatcaagagc taccaactct    3660
ttttccgaag gtaactggct tcagcagagc gcagatacca atactgtcc ttctagtgta    3720 gccgtagtta ggccaccact tcaagaactc tgtagcaccg cctacatacc tcgctctgct    3780
aatcctgtta ccagtggctg ctgccagtgg cgataagtcg tgtcttaccg ggttggactc    3840
aagacgatag ttaccggata aggcgcagcg gtcgggctga acgggggtt cgtgcacaca    3900 gcccagcttg gagcgaacga cctacaccga actgagatac ctacagcgtg agctatgaga    3960
aagcgccacg cttcccgaag ggagaaaggc ggacaggtat ccggtaagcg gcagggtcgg    4020
aacaggagag cgcacgaggg agcttccagg gggaaacgcc tggtatcttt atagtcctgt    4080
cgggtttcgc cacctctgac ttgagcgtcg attttttgtga tgctcgtcag ggggggcgga    4140
cctatggaaa aacgccagca acgcggcctt tttacggttc ctggcctttt gctggccttt    4200
tgctcacatg ttctttcctg cgttatcccc tgattctgtg ataaccgta ttaccgcctt    4260 tgagtgagct gataccgctc gccgcagccg aacgaccgag cgcagcgagt cagtgagcga    4320
ggaagcggaa gagcgcctga tgcggtattt tctccttacg catctgtgcg gtatttcaca    4380
ccgcatatat ggtgcactct cagtacaatc tgctctgatg ccgcatagtt aagccagtat    4440
acactccgct atcgctacgt gactgggtca tggctgcgcc ccgacacccg ccaacacccg    4500
ctgacgcgcc ctgacgggct tgtctgctcc cggcatccgc ttacagacaa gctgtgaccg    4560
tctccgggag ctgcatgtgt cagaggtttt caccgtcatc accgaaacgc gcgaggcagc    4620
tgcggtaaag ctcatcagcg tggtcgtgaa gcgattcaca gatgtctgcc tgttcatccg    4680
```

| | |
|---|---|
| cgtccagctc gttgagtttc tccagaagcg ttaatgtctg gcttctgata aagcgggcca | 4740 |
| tgttaagggc ggttttttcc tgtttggtca cttgatgcct ccgtgtaagg gggaatttct | 4800 |
| gttcatgggg gtaatgatac cgatgaaacg agagaggatg ctcacgatac gggttactga | 4860 |
| tgatgaacat gcccggttac tggaacgttg tgagggtaaa caactggcgg tatggatgcg | 4920 |
| gcgggaccag agaaaaatca ctcagggtca atgccagcgc ttcgttaata cagatgtagg | 4980 |
| tgttccacag ggtagccagc agcatcctgc gatgcagatc cggaacataa tggtgcaggg | 5040 |
| cgctgacttc cgcgttttcca gactttacga aacacggaaa ccgaagacca ttcatgttgt | 5100 |
| tgctcaggtc gcagacgttt tgcagcagca gtcgcttcac gttcgctcgc gtatcggtga | 5160 |
| ttcattctgc taaccagtaa ggcaaccccg ccagcctagc cgggtcctca acgacaggag | 5220 |
| cacgatcatg cgcacccgtg gccaggaccc aacgctgccc gagatgcgcc gcgtgcggct | 5280 |
| gctggagatg gcggacgcga tggatatgtt ctgccaaggg ttggtttgcg cattcacagt | 5340 |
| tctccgcaag aattgattgg ctccaattct tggagtggtg aatccgttag cgaggtgccg | 5400 |
| ccggcttcca ttcaggtcga ggtggcccgg ctccatgcac cgcgacgcaa cgcggggagg | 5460 |
| cagacaaggt atagggcggc gcctacaatc catgccaacc cgttccatgt gctcgccgag | 5520 |
| gcggcataaa tcgccgtgac gatcagcggt ccagtgatcg aagttaggct ggtaagagcc | 5580 |
| gcgagcgatc cttgaagctg tccctgatgg tcgtcatcta cctgcctgga cagcatggcc | 5640 |
| tgcaacgcgg gcatcccgat gccgccggaa gcgagaagaa tcataatggg gaaggccatc | 5700 |
| cagcctcgcg tcgcgaacgc cagcaagacg tagcccagcg cgtcggccgc catgccggcg | 5760 |
| ataatggcct gcttctcgcc gaaacgtttg gtggcgggac cagtgacgaa ggcttgagcg | 5820 |
| agggcgtgca agattccgaa taccgcaagc gacaggccga tcatcgtcgc gctccagcga | 5880 |
| aagcggtcct cgccgaaaat gacccagagc gctgccggca cctgtcctac gagttgcatg | 5940 |
| ataaagaaga cagtcataag tgcggcgacg atagtcatgc cccgcgccca ccggaaggag | 6000 |
| ctgactgggt tgaaggctct caagggcatc ggtcgacgct ctcccttatg cgactcctgc | 6060 |
| attaggaagc agcccagtag taggttgagg ccgttgagca ccgccgccgc aaggaatggt | 6120 |
| gcatgcatgc atcgaaatta atacgacgaa attaatacga ctcactatag gcaattgcg | 6180 |
| atcaccacaa ttcagcaaat tgtgaacatc atcacgttca tctttccctg gttgccaatg | 6240 |
| gcccattttc ctgtcagtaa cgagaaggtc gcgaattcag gcgcttttta gactggtcgt | 6300 |
| aatgaac | 6307 |

<210> SEQ ID NO 25
<211> LENGTH: 6191
<212> TYPE: DNA
<213> ORGANISM: E. coli, Rhodococcus opacus

<400> SEQUENCE: 25

| | |
|---|---|
| aattcttaag aaggagatat acatatgacg attactacca cttcgccaag gcagatcgcc | 60 |
| ggtcggtgga cacgtgccga gcggcaacga ctgagcgcta tcatcggcac catcgcattg | 120 |
| ctgcacgtgc taggtatcgc aatgtatctc gggcgctcgg gtaacccggc cgccgctggt | 180 |
| agcctggctg gctcgggact gctcgcctat gtcctgggtg cgcggcacgc gttcgatgcc | 240 |
| gaccacatcg cggccatcga cgacaccacc cgcatcatgc tccttcgcgg acgccgaccc | 300 |
| gtcggcgtcg gattcttttt cgccatgggg cattcgactg tcgtcctcgt tctctctctg | 360 |
| atcgtcgctt tcggagcggg ctcgctcagt tcgatggaag cgtcccgggt cgaggagatc | 420 |

-continued

```
ggaggttacg tcgcgacctg cgtggcagtg ctgttcttgg tgctggtggc cgcactcaac    480
agtttcgttc tgcgcaagct cctcgctctg tctcgtcgga tgcgcactgg ggaagatatc    540
tccggcgacc tcgagcgcgg gctgggtgaa cggggattgc tcagctggct tctcagcggc    600
cgattgcgcg ggctgattcg ttcgtcctgg cacatgtacc cggtgggcct gctcatgggt    660
ctcggcctgg aaaccgcatc cgaagtgaca ttgctgtctc tcactgcctc cgcagcgagc    720
ggaggtcagc tatcgctaat ggcgattgtg agccttccat tgttgtttgc cgcggggatg    780
agcaccttcg atactgcaga ctcactcgtc atgacccgcg cctattcgtg gtcctataac    840
gatgcccagc gccgccttcg cttcaacact gtaaccacgg gtgcgaccat ggtcatcggg    900
ttcttcgtcg cgggaatcta cgtttctgga ctgcttgcgc cgctaccagg gttcggttgg    960
ctgacccctc tgggcgcgat cgccgacaac ttcgagttcc tcggctacgc agtcgccgga   1020
ttgttcgttg ctacctgggc aatcgcagca ctggttagcc ggcctcgacg gcttgtcggc   1080
agctcgaagg tgtgagatgt cggtaccaag cttggctgtt ttggcggatg agagaagatt   1140
ttcagcctga tacagattaa atcagaacgc agaagcggtc tgataaaaca gaatttgcct   1200
ggcggcagta gcgcggtggt cccacctgac cccatgccga actcagaagt gaaacgccgt   1260
agcgccgatg gtagtgtggg gtctccccat gcgagagtag ggaactgcca ggcatcaaat   1320
aaaacgaaag gctcagtcga aagactgggc ctttcgtttt atctgttgtt tgtcggtgaa   1380
cgctctcctg agtaggacaa atccgccggg agcggatttg aacgttgcga agcaacggcc   1440
cggagggtgg cgggcaggac gcccgccata aactgccagg catcaaatta gcagaaggc    1500 catcctgacg gatggccttt tgcgtttct acaaactctt ttgttattt ttctaaatac    1560 attcaaatat gtatccgctc atgagacaat aaccctgata aatgcttcaa taatatcgtc   1620
cattccgaca gcatcgccag tcactatggc gtgctgctag cgctatatgc gttgatgcaa   1680
tttctatgcg cacccgttct cggagcactg tccgaccgct ttggccgccg cccagtcctg   1740
ctcgcttcgc tacttggagc cactatcgac tacgcgatca tggcgaccac accgtcctg   1800 tggatcctct acgccggacg catcgtggcc ggcatcaccg cgccacagg tgcggttgct    1860 ggcgcctata tcgccgacat caccgatggg gaagatcggg ctcgccactt cgggctcatg   1920
agcgcttgtt tcggcgtggg tatggtggca ggccccgtgg ccgggggact gttgggcgcc   1980 atctcccttgc atgcaccatt ccttgcggcg gcggtgctca acggcctcaa cctactactg   2040
ggctgcttcc taatgcagga gtcgcataag ggagagcgtc gaccgatgcc cttgagagcc   2100
ttcaacccag tcagctcctt ccggtgggcg cggggcatga ctatcgtcgc cgcacttatg   2160
actgtcttct ttatcatgca actcgtagga caggtgccgg cagcgctctg gtcattttc    2220 ggcgaggacc gctttcgctg gagcgcgacg atgatcggg tgtcgcttgc ggtattcgga    2280
atcttgcacg ccctcgctca agccttcgtc actggtcccg ccaccaaacg tttcggcgag   2340
aagcaggcca ttatcgccgg catggcggcc gacgcgctgg gctacgtctt gctggcgttc   2400
gcgacgcgag gctggatggc cttccccatt atgattcttc tcgcttccgg cggcatcggg   2460
atgcccgcgt tgcaggccat gctgtccagg caggtagatg acgaccatca gggacagctt   2520
caaggatcgc tcgcggctct taccagccta acttcgatca ctggaccgct gatcgtcacg   2580
gcgatttatg ccgcctcggc gagcacatgg aacgggttgg catggattgt aggcgccgcc   2640
ctataccttg tctgcctccc cgcgttgcgt cgcggtgcat ggagccgggc cacctcgacc   2700
tgaatggaag ccggcggcac ctcgctaacg gattcaccac tccaagaatt ggagccaatc   2760
aattcttgcg gagaactgtg aatgcgcaaa ccaacccttg gcagaacata tccatcgcgt   2820
```

-continued

```
ccgccatctc cagcagccgc acgcggcgca tctcgggcag cgttgggtcc tggccacggg    2880
tgcgcatgat cgtgctcctg tcgttgagga cccggctagg ctggcggggt tgccttactg    2940
gttagcagaa tgaatcaccg atacgcgagc gaacgtgaag cgactgctgc tgcaaaacgt    3000
ctgcgacctg agcaacaaca tgaatggtct tcggtttccg tgtttcgtaa agtctggaaa    3060
cgcggaagtc ccctacgtgc tgctgaagtt gcccgcaaca gagagtggaa ccaaccggtg    3120
ataccacgat actatgactg agagtcaacg ccatgagcgg cctcatttct tattctgagt    3180
tacaacagtc cgcaccgctg tccggtagct ccttccggtg ggcgcggggc atgactatcg    3240
tcgccgcact tatgactgtc ttctttatca tgcaactcgt aggacaggtg ccggcagcgc    3300
ccaacagtcc cccggccacg gggcctgcca ccatacccac gccgaaacaa gcgccctgca    3360
ccattatgtt ccggatctgc atcgcaggat gctgctggct accctgtgga cacctacat    3420 ctgtattaac gaagcgctaa ccgttttat caggctctgg gaggcagaat aaatgatcat    3480
atcgtcaatt attacctcca cggggagagc ctgagcaaac tggcctcagg catttgagaa    3540
gcacacggtc acactgcttc cggtagtcaa taaaccggta aaccagcaat agacataagc    3600
ggctatttaa cgaccctgcc ctgaaccgac gaccgggtcg aatttgcttt cgaatttctg    3660
ccattcatcc gcttattatc acttattcag gcgtagcacc aggcgtttaa gggcaccaat    3720
aactgcctta aaaaaattac gccccgccct gccactcatc gcagtactgt tgtaattcat    3780
taagcattct gccgacatgg aagccatcac agacggcatg atgaacctga atcgccagcg    3840
gcatcagcac cttgtcgcct tgcgtataat atttgcccat ggtgaaaacg ggggcgaaga    3900
agttgtccat attggccacg tttaaatcaa aactggtgaa actcacccag ggattggctg    3960
agacgaaaaa catattctca ataaaccctt tagggaaata ggccaggttt tcaccgtaac    4020
acgccacatc ttgcgaatat atgtgtagaa actgccggaa atcgtcgtgg tattcactcc    4080
agagcgatga aaacgtttca gtttgctcat ggaaaacggt gtaacaaggg tgaacactat    4140
cccatatcac cagctcaccg tctttcattg ccatacgaat tccggatgag cattcatcag    4200
gcgggcaaga atgtgaataa aggccggata aaacttgtgc ttattttct ttacggtctt    4260 taaaaaggcc gtaatatcca gctgaacggt ctggttatag gtacattgag caactgactg    4320
aaatgcctca aaatgttctt tacgatgcca ttgggtatat caacggtgg tatatccagt    4380 gatttttttc tccattttag cttccttagc tcctgaaaat ctcgataact caaaaaatac    4440
gcccggtagt gatcttattt cattatggtg aaagttggaa cctcttacgt gccgatcaac    4500
gtctcatttt cgccaaaagt tggcccaggg cttcccggta tcaacaggga caccaggatt    4560
tatttattct gcgaagtgat cttccgtcac aggtatttat tcggcgcaaa gtgcgtcggg    4620
tgatgctgcc aacttactga tttagtgtat gatggtgttt ttgaggtgct ccagtggctt    4680
ctgtttctat cagctgtccc tcctgttcag ctactgacgg ggtggtgcgt aacggcaaaa    4740
gcaccgccgg acatcagcgc tagcggagtg tatactggct tactatgttg gcactgatga    4800
gggtgtcagt gaagtgcttc atgtggcagg agaaaaaagg ctgcaccggt gcgtcagcag    4860
aatatgtgat acaggatata ttccgcttcc tcgctcactg actcgctacg ctcggtcgtt    4920
cgactgcggc gagcggaaat ggcttacgaa cggggcggag atttcctgga agatgccagg    4980
aagatactta acagggaagt gagagggccg cggcaaagcc gttttccat aggctccgcc    5040 cccctgacaa gcatcacgaa atctgacgct caaatcagtg gtggcgaaac ccgacaggac    5100
tataaagata ccaggcgttt cccctggcgg ctccctcgtg cgctctcctg ttcctgcctt    5160
```

-continued

```
tcggtttacc ggtgtcattc cgctgttatg gccgcgtttg tctcattcca cgcctgacac    5220
tcagttccgg gtaggcagtt cgctccaagc tggactgtat gcacgaaccc cccgttcagt    5280
ccgaccgctg cgccttatcc ggtaactatc gtcttgagtc caacccggaa agacatgcaa    5340
aagcaccact ggcagcagcc actggtaatt gatttagagg agttagtctt gaagtcatgc    5400
gccggttaag gctaaactga aaggacaagt tttggtgact gcgctcctcc aagccagtta    5460
cctcggttca aagagttggt agctcagaga accttcgaaa aaccgccctg caaggcggtt    5520
ttttcgtttt cagagcaaga gattacgcgc agaccaaaac gatctcaaga agatcatctt    5580
attaagcttg catgcctgca ggacggatcc ccgggtaccg agctcgaatt taatcagata    5640
aaatatttca agatttcagt gcaatttatc tcttcaaatg tagcacctga agtcagcccc    5700
atacgatata agttgtaatt ctcatgtttg acagcttatc atcgataagc tttaatgcgg    5760
tagtttatca cagttaaatt gctaacgcag tcaggcaccg tgtatgaaat ctaacaatgc    5820
gctcatcgtc atcctcggca ccgtcaccct ggatgctgta ggcataggct tggttatgcc    5880
ggtactgccg ggcctcttgc gggattagtc atgccccgcg cccaccggaa ggagctgact    5940
gggttgaagg ctctcaaggg catcggtcga cgctctccct tatgcgactc ctgcattagg    6000
aagcagccca gtagtaggtt gaggccgttg agcaccgccg ccgcaaggaa tggtgcatgc    6060
atcgatcacc acaattcagc aaattgtgaa catcatcacg ttcatctttc cctggttgcc    6120
aatggcccat tttcctgtca gtaacgagaa ggtcgcgaat tcaggcgctt tttagactgg    6180
tcgtaatgaa c                                                         6191
```

RHODOCOCCUS NITRILE HYDRATASE

CROSS REFERENCE TO RELATED APPLICATIONS

The present application is a division of U.S. application Ser. No. 11/083,327, filed Mar. 18, 2005 now U.S. Pat. No. 7,288,402. U.S. Pat. No. 11/083,327 claims priority to German application Ser. No. 10 2004 013 824.9, filed on Mar. 20, 2004. These previous applications are incorporated by reference herein in their entirety.

The invention relates to a *Rhodococcus* polynucleotide cluster which contains nucleotide sequences which encode polypeptides having the activity of a nitrile hydratase, of an auxiliary protein P15K which activates this enzyme, and of a cobalt transporter, to microorganisms which are transformed with this cluster and in which the nucleotide sequences encoding these proteins are present in increased quantity, and to the use of the transformed microorganisms for preparing amides from nitriles.

A large number of nitrile hydratases have already been described in the literature (Synthetic applications of nitrile-converting enzymes; Martinkova, Ludmila; Mylerova, Veronika; Current Organic Chemistry (2003), 7(13), 1279-1295). Nitrile hydratases have been used since 1983 for producing acrylamide on a scale of several thousand tons per year. This biocatalytic process has proved to be able to compete with the chemical processes (Enzymic synthesis of acrylamide: a success story not yet over; Kobayashi, Michihiko; Nagasawa, Toru; Yamada, Trends in Biotechnology (1992), 10(11), 402-8).

In addition to the nitrile hydratases which can be used for converting acrylonitrile, nitrile hydratases which are are particularly suitable for converting methacrylonitrile (A nitrile hydratase of Pseudonocardia thermophila and the genes encoding and manufacture of the enzyme for conversion of nitriles to amides (EP 790310), 3-cyanopyridine (Process for producing amides with *Rhodococcus* nitrile hydratase (WO 2002055670) or 2-hydroxynitriles such as 2-hydroxy-4-methylthiobutyro-nitrile (A nitrile hydratase of *Rhodococcus* and its use in the manufacture of amides (WO 2002070717) and Enzymic conversion of α-hydroxynitriles to the corresponding α-hydroxyamides, acids or acid salts, (WO 9832872) have, for example, also been described. By contrast, no nitrile hydratases which can be used to efficiently convert 2-aminonitriles are thus far known. While the *Rhodococcus* sp. Cr4 nitrile hydratase converts 2-hydroxynitriles, for example, with a high degree of activity, it does not convert a simple 2-aminonitrile such as aminoacetonitrile at all (WO 2002070717).

The enzymic conversion of aminonitriles into the corresponding amides opens up an attractive route for synthesizing amino acids since 2-aminoamides can be hydrolyzed readily (WO 2001060789). This process proceeds under mild conditions and with a very high degree of selectivity and without the formation of byproducts such as salts, as accrue in connection with chemical hydrolysis.

Alternatively, amides can also be converted with alkali metal or alkaline earth metal hydroxides into the corresponding salts of the acids. This approach is particularly preferred when using calcium hydroxide for converting 4-methylthio-α-hydroxybutyramide (MHA-amide), since the calcium salt of MHA can be used directly as a feedstuff additive, as a product form which is an alternative to methionine or MHA.

However, for producing a commodity product such as DL-methionine, it is not sufficient to make available a high-activity biocatalyst. In order to increase the activity, it is necessary to establish a system for expressing the genes which are to be amplified. One possibility which presents itself is heterologous expression, for example, and in particular, in *Escherichia coli, Bacillus, Pseudomonas, Pichia, Sacharomyces* or *Aspergillus*, since these microorganisms exhibit rapid growth, achieve very high cell densities and are available molecular biological tools which permit very high expression levels (Lee S Y (1996) High cell-density culture of *Escherichia coli*. TIBTECH 14:98-105; Riesenberg D, Guthke R (1999) High-cell-density cultivation of microorganisms. Appl Microbiol Biotechnol 51:422-430).

It is known that at least 3 genes have to be coexpressed for nitrile hydratases to be expressed heterologously. In addition to two structural genes, a corresponding auxiliary protein has to be amplified both for iron-dependent and for cobalt-dependent enzymes (Nojiri M. et al., (1999) Functional expression of Nitrile hydratases in *Escherichia coli*: Requirement of a nitrile hydratase activator and a post-translational modification of a ligand cysteine. J Biochem 125: 696-704 and Over-production of stereoselective nitrile hydratase from *Pseudomonas putida* 5B in *Escherichia coli*: activity requires a novel downstream protein, Wu, S.; Fallon, R. D.; Payne, M. S. Applied Microbiology and Biotechnology (1997), 48(6), 704-708).

In addition to these 3 genes, a further gene, which encodes a cobalt transporter, was found, alongside the structural genes and the auxiliary protein gene, in a gene cluster in *Rhodococcus rhodochrous* J1 (A novel transporter involved in cobalt uptake, Komeda, Hidenobu et al., Proceedings of the National Academy of Sciences of the United States of America (1997), 94(1), 36-41). Over-expression in both *Rhodococcus* and in *E. coli* leads to an increased uptake of $Co^{2+}$ ions from the culture medium. In addition, it was shown that, when the cobalt transporter is coexpressed together with the 3 other proteins, it is possible to achieve the same nitrile hydratase activity at a concentration of Co in the medium which is lower than when the structural genes and the auxiliary protein are expressed on their own. However, according to Komeda et al., this effect only occurs in *Rhodococcus* at concentrations of less than 42 μM.

EP 0 362 829 discloses the fermentation of *Rhodococcus rhodochrous* in the presence of cobalt salts.

The object of the invention is to make available nitrile hydratases which possess high activity and which, in particular, convert α-aminonitriles into amides.

The invention relates to the following:

1. Isolated polynucleotide clusters, from *Rhodococcus*, especially from *Rhodococcus opacus* which contain four nucleotide sequences which encode four polypeptides which possess amino acid sequences which are in each case at least 90% identical to the amino acid sequences contained in the sequences SEQ ID NO:2 to SEQ ID NO:5, with the polypeptides possessing the activities of a nitrile hydratase, composed of an α subunit and a β subunit, of the auxiliary protein P15K and of a cobalt transporter.
2. Polynucleotides, selected from the group:
    a) polynucleotide consisting of positions 1 to 708 in the nucleotide sequence SEQ ID NO:1 or in the nucleotide sequence which is complementary thereto,
    b) polynucleotide possessing a nucleotide sequence which corresponds to the sequence from a) within the bounds of the degeneracy of the genetic code,
    c) polynucleotide which hybridizes, under stringent conditions, with the complementary sequences a) or b), and
    d) polynucleotide possessing a nucleotide sequence from a), b) or c) which contains functionally neutral sense mutations, with the polynucleotides encoding the β subunit of the nitrile hydratase.
3. Polynucleotides, selected from the group:
   a) polynucleotide comprising positions 710 to 1327 in the nucleotide sequence SEQ ID NO:1 or in the nucleotide sequence which is complementary thereto,
   b) polynucleotide possessing a nucleotide sequence which corresponds to the sequence from a) within the bounds of the degeneracy of the genetic code,
   c) polynucleotide which hybridizes, under stringent conditions, with the complementary sequences a) or b), and
   d) polynucleotide possessing a nucleotide sequence from a), b) or c) which contains functionally neutral sense mutations,
   with the polynucleotides encoding the α subunit of the nitrile hydratase.
4. Polynucleotides, selected from the group:
   a) polynucleotide comprising positions 1324 to 1737 in the nucleotide sequence SEQ ID NO:1 or in the nucleotide sequence which is complementary thereto,
   b) polynucleotide possessing a nucleotide sequence which corresponds to the sequence from a) within the bounds of the degeneracy of the genetic code,
   c) polynucleotide which hybridizes, under stringent conditions, with the complementary sequences a) or b), and
   d) polynucleotide possessing a nucleotide sequence from a), b) or c) which contains functionally neutral sense mutations,
   with the polynucleotides encoding the auxiliary protein P15K.
5. Polynucleotides, selected from the group:
   a) polynucleotide comprising positions 2076 to 3146 in the nucleotide sequence SEQ ID NO:1 or in the nucleotide sequence which is complementary thereto,
   b) polynucleotide possessing a nucleotide sequence which corresponds to the sequence from a) within the bounds of the degeneracy of the genetic code,
   c) polynucleotide which hybridizes, under stringent conditions, with the complementary sequences a) or b), and
   d) polynucleotide possessing a nucleotide sequence from a), b) or c) which contains functionally neutral sense mutations,
   with the polynucleotides encoding a protein which has the activity of a cobalt transporter.
6) Polypeptide according to 2) or 3) which contains the amino acid sequences SEQ ID NO:2 and SEQ ID NO:3, with the polypeptide exhibiting the activity of a nitrile hydratase.
7) Polypeptide according to 4) which contains the amino acid sequence SEQ ID NO:6, with the polypeptide exhibiting the activity of the auxiliary protein P15 K.
8) Polypeptide according to 5) which contains the amino acid sequence SEQ ID NO:5, with the polypeptide exhibiting the activity of a cobalt transporter.
9) Probe or primer, which contains at least 20 consecutive nucleotides within positions 1 to 1327 from the nucleotide sequence SEQ ID NO:1 or its complementary form.
10) Probe or primer, which contains at least 20 consecutive nucleotides within positions 1324 to 1737 from the nucleotide sequence SEQ ID NO:1 or its complementary form.
11) Probe or primer, which contains at least 20 consecutive nucleotides within positions 2076 to 3146 from the nucleotide sequence SEQ ID NO:1 or its complementary form.
12) Isolated polynucleotide according to 2) and 3) which hybridizes, under stringent conditions, with the complement comprising positions 1 to 1327 from SEQ ID NO:1, with the stringent conditions comprising washing in 5×SSC at a temperature of from 50 to 68° C.
13) Isolated polynucleotide according to 4) which hybridizes, under stringent conditions, with the complement comprising positions 1324 to 1737 from SEQ ID NO:1, with the stringent conditions comprising washing in 5×SSC at a temperature of from 50 to 68° C.
14) Isolated polynucleotide according to 5), which hybridizes, under stringent conditions, with the complement comprising positions 2076 to 3146 from SEQ ID NO:1, with the stringent conditions comprising washing in 5×SSC at a temperature of from 50 to 68° C.
15) Vectors which contain (a) polynucleotide(s) selected from 1) to 5) and 12) to 14), or according to 2), 3) and 4) or according to 5).
16) Vector pUD15, comprising the nucleotide sequence SEQ ID No. 24, containing the sequences according to 2), 3), and 6) from SEQ ID NO:1, with the start codon gtg having been changed to atg.
17) Vector pUD16, comprising the nucleotide sequence SEQ ID NO:25, containing the sequence according to 5), with the start codon ttg having been changed to atg.
18) Host cell, which is transformed or transfected by introducing a polynucleotide according to 1) to 5) and 12) to 14). The host cell can be a eukaryote or prokaryote which is known to have an expression system of adequate stability.
19) Host cell, which is transformed by introducing a vector according to 15) to 17).
20) Transformed host cell according to 18) or 19), with the host cell being a bacterium of the family Enterobacteriaceae, in particular *Escherichia*.

Vector DNA can be introduced into eukaryotic or prokaryotic cells using known transformation or transfection techniques.

"Transformation", "transfection", "conjugation" and "transduction" refer to procedures for introducing foreign DNA which are known in the prior art.

The invention also relates to polynucleotides which are essentially composed of a polynucleotide sequence which can be obtained by using hybridization to screen an appropriate *Rhodococcus opacus* gene library which contains the complete gene, or parts thereof, with a probe which contains the sequences of the polynucleotides according to the invention from SEQ ID No:1, or fragments thereof, and isolating said polynucleotide sequence.

Polynucleotides which contain the sequences according to the invention are suitable for use as hybridization probes for RNA, cDNA and DNA, for the purpose of isolating nucleic acids or polynucleotides or full-length genes which encode the proteins according to the invention or for the purpose of isolating nucleic acids or polynucleotides or genes whose sequences exhibit a high degree of similarity with those of the genes according to the invention. They can also be applied, as probes, on what are termed arrays, microarrays or DNA chips for the purpose of detecting and determining the corresponding polynucleotides or sequences, such as RNA or cDNA, which are derived therefrom.

Polynucleotides which contain the sequences according to the invention are also suitable for use as primers which can be used, together with the polymerase chain reaction (PCR), to prepare DNA from genes which encode the proteins according to the invention.

These oligonucleotides, which serve as probes or primers, contain at least 25 or 30, preferably at least 20, very particularly preferably at least 15, consecutive nucleotides. Oligonucleotides having a length of at least 40 or 50 nucleotides are likewise suitable. Where appropriate, oligonucleotides having a length of at least 100, 150, 200, 250 or 300 nucleotides are also suitable.

"Isolated" means taken out of its natural environment. In general, "polynucleotide" refers to polyribonucleotides and polydeoxyribonucleotides, with it being possible for the RNA or DNA to be unmodified or modified.

The polynucleotides according to the invention encompass polynucleotides as depicted in SEQ ID No. 1, or fragments contained therein, and also polynucleotides which are at least 90%, 93%, 95%, 97% or 99% identical to the polynucleotides as depicted in SEQ ID NO:1 or fragments contained therein.

"Polypeptides" are understood as being peptides or proteins which contain two or more amino acids which are linked by way of peptide bonds.

The polypeptides according to the invention encompass a polypeptide as depicted in the sequences SEQ ID NO:2 to SEQ ID NO:4 and SEQ ID NO:6 and also polypeptides which are at least 90%, and particularly preferably at least 91%, 95%, 97% or 99%, identical to the polypeptides as depicted in the sequences SEQ ID NO:2 to SEQ ID NO: 4 and SEQ ID NO:6.

The SEQ ID NO:1 polynucleotides contain several individual sequences which encode different proteins. The sequences for the α subunit and the auxiliary protein P15K overlap each other.

The genes which encode the α subunit and the β subunit of nitrile hydratase have to be expressed jointly in order to obtain an active protein.

SEQ ID NO:2 depicts the amino acid sequence of the β subunit, and SEQ ID NO:3 depicts that of the α subunit, of the protein which exhibits nitrile hydratase activity.

SEQ ID NO:2 is derived from positions 1 to 708, and SEQ ID NO:3 is derived from positions 710 to 1327, of the nucleotide sequence SEQ ID NO:1.

The amino acid sequence of the auxiliary protein P15K is to be found in SEQ ID NO:6, corresponding to positions 1324 to 1737 in the nucleotide sequence SEQ ID NO:1.

The auxiliary protein activates the nitrile hydratase and has to be present, together with this enzyme, in the microorganism which is forming the nitryl hydratase.

SEQ ID NO:4 stands for the amino acid sequence of the cobalt transporter and is derived from positions 2076 to 3146 of the nucleotide sequence SEQ ID NO:1.

PatentIN Version 3.1 translates the start codon ttg in SEQ ID NO:4 as leucine and translates the start codon gtg in SEQ ID NO:6 as valine. The correct amino acid is methionine.

It has been found that the nitrile hydratase activity in *E. coli* is increased many times over by coexpressing the cobalt transporter. This is also the case when high concentrations of cobalt are used in the medium, with these concentrations being orders of size above the concentrations which occur naturally. Surprisingly, coexpressing the cobalt transporter does not lead to any poisoning of the organism but only to a slightly increased sensitivity of the cells towards high cobalt concentrations in the medium.

In order to isolate the gene cluster according to the invention, a gene library of this microorganism is generally first of all prepared in *Escherichia coli* (*E. coli*). The preparation of gene libraries is described in well-known textbooks and manuals. Examples which may be mentioned are the textbook by Winnacker: Gene und Klone, Eine Einführung in die Gentechnologie [Genes and clones, an introduction to recombinant DNA technology] (Verlag Chemie, Weinheim, Germany, 1990) or the manual by Sambrook et al.: Molecular Cloning, A Laboratory Manual (Cold Spring Harbor Laboratory Press, 1989). A very well known gene library is that of the *E. coli* K-12 strain W3110, which was prepared by Kohara et al. (Cell 50, 495-508 (1987)) in λ vectors. Bathe et al. (Molecular and General Genetics, 252:255-265, 1996) describe a gene library of *C. glutamicum* ATCC13032, which was prepared in the *E. coli* K-12 strain NM554 (Raleigh et al., 1988, Nucleic Acids Research 16:1563-1575) using the cosmid vector SuperCos I (Wahl et al., 1987, Proceedings of the National Academy of Sciences USA, 84:2160-2164).

It is also possible to use plasmids such as pBR322 (Bolivar, Life Sciences, 25, 807-818 (1979)) or pUC9 (Vieira et al., 1982, Gene, 19:259-268) for preparing a gene library in *E. coli*. Suitable hosts are, in particular, *E. coli* strains which are restriction defective and recombination defective. An example of these strains is the strain DH5αmcr, which has been described by Grant et al. (Proceedings of the National Academy of Sciences USA, 87 (1990) 4645-4649). The long DNA fragments which have been cloned using cosmids can then in turn be subcloned into common vectors which are suitable for sequencing and then sequenced as described, for example, in Sanger et al. (Proceedings of the National Academy of Sciences of the United States of America, 74:5463-5467, 1977).

The resulting DNA sequences can then be investigated using known algorithms or sequence analysis programs such as that of Staden (Nucleic Acids Research 14, 217-232 (1986)), that of von Marck (Nucleic Acids Research 16, 1829-1836 (1988)) or the GCG program of Butler (Methods of Biochemical Analysis 39, 74-97 (1998)).

Coding DNA sequences which ensue from the sequences contained in from SEQ ID No. 1 as a result of the degeneracy of the genetic code likewise form part of the subject matter of the invention. In the same way, DNA sequences which hybridize with these sequences, or parts thereof, form part of the subject matter of the invention. Furthermore, conservative amino acid substitutions, such as the replacement of glycine with alanine, or of aspartic acid with glutamic acid, in proteins are known in the field as sense mutations which do not lead to any fundamental change in the activity of the protein, i.e. are functionally neutral. It is furthermore known that changes at the N terminus and/or C terminus of a protein may not significantly impair the function of the protein or may even stabilize it. The skilled person can find information in this regard in, inter alia, Ben-Bassat et al. (Journal of Bacteriology 169:751-757 (1987)), O'Regan et al. (Gene 77:237-251 (1989)), Sahin-Toth et al. (Protein Sciences 3:240-247 (1994)), and in Hochuli et al. (Bio/Technology 6:1321-1325 (1988)) and in known textbooks of genetics and molecular biology.

Finally, DNA sequences which are prepared by the polymerase chain reaction (PCR) using primers which ensue from SEQ ID NO: 1 also form part of the subject matter of the invention. These oligonucleotides typically have a length of at least 15 nucleotides.

The skilled person can find instructions for identifying DNA sequences by means of hybridization in, inter alia, the manual "The DIG System Users Guide for Filter Hybridization" published by the company Boehringer Mannheim GmbH (Mannheim, Germany, 1993) and in Liebl et al. (International Journal of Systematic Bacteriology (1991) 41: 255-260). The hybridization takes place under stringent conditions, i.e. the only hybrids to be formed are those in which the probe and target sequence, i.e. the polynucleotides treated with the probe, are at least 90% identical. It is known that the stringency of the hybridization, including the washing steps, is influenced or determined by varying the buffer composition, the temperature and the salt concentration. The hybridization reaction is preferably carried out at a stringency which is relatively low as compared with that of the washing steps (Hybaid Hybridisation Guide, Hybaid Limited, Teddington, UK, 1996).

For example, a 5×SSC buffer can be used, at a temperature of approx. 50° C.-68° C., for the hybridization reaction. Under these conditions, probes can also hybridize with polynucleotides which exhibit less than 70% identity with the sequence of the probe. These hybrids are less stable and are removed by washing under stringent conditions. This can, for example, be achieved by lowering the salt concentration down to 2×SSC and, where appropriate, subsequently to 0.5× SSC (The DIG System User's Guide for Filter Hybridisation, Boehringer Mannheim, Mannheim, Germany, 1995), with the temperature being set at approx. 50° C.-68° C. It is possible, where appropriate, to lower the salt concentration down to 0.1×SSC. By increasing the hybridization temperature stepwise from 50° C. to 68° C. in steps of approx. 1-2° C., it is possible to isolate polynucleotide fragments which possess, for example, at least 90% to 95% identity with the sequence of the probe which is employed. Further hybridization instructions can be obtained on the market in the form of kits (e.g. DIG Easy Hyb supplied by Roche Diagnostics GmbH, Mannheim, Germany, Catalog No. 1603558).

The skilled person can find instructions for amplifying DNA sequences using the polymerase chain reaction (PCR) in, inter alia, the manual by Gait: Oligonucleotide synthesis: A Practical Approach (IRL Press, Oxford, UK, 1984) and in Newton and Graham: PCR (Spektrum Akademischer Verlag, Heidelberg, Germany, 1994).

In general, the approach is to clone a gene which is expressed at a high level into a vector having a low copy number and to clone genes which are expressed more weakly into a vector with a higher copy number and/or a strong promoter. The host cells are transformed with these vectors such that they then in each case contain at least one additional copy, as compared with the starting organism, of the nucleotide sequences which encode the formation of nitrile hydratase or of the other proteins.

It has been found to be advantageous to express the cobalt transporter-encoding gene at a lower level, for example using a vector of low copy number, i.e. at least one copy less, than that for the polynucleotide sequences which encode the α and β subunits and the P15K auxiliary protein. Differential expression of said genes can also be achieved by using promoters of differing strength.

The nucleotides encoding the α and β subunits, on the one hand, and the auxiliary protein, on the other hand, are preferably located jointly on one vector and either share a common promoter or have two separate promoters.

The transformed or recombinant microorganisms which have been prepared in this way likewise form part of the subject matter of the invention.

It has been found that amplifying the genes encoding the nitrile hydratase, the P15K auxiliary protein and the cobalt transporter in microorganisms leads to an increased production of the nitrile hydratase or else to an increased activity of the nitrile hydratase.

In this connection, the term "amplification" describes the increase in the intracellular activity, in a micro-organism, of one or more enzymes, which are encoded by the corresponding DNA, which is acheived by, for example, increasing the copy number of the gene or genes, using a strong promoter or using a gene which encodes a corresponding enzyme having a high activity, and, where appropriate, combining these measures.

In order to achieve overexpression, the promoter and regulatory region or the ribosomal binding site, which is located upstream of the structural gene, can be mutated. Expression cassettes which are incorporated upstream of the structural gene act in the same manner. In addition, it is possible, by using inducible promoters, to increase expression during the course of the fermentative amino acid production. Expression is likewise improved by measures taken to extend the lifetime of the mRNA.

In addition, the enzyme activity is also augmented by preventing the enzyme protein from being broken down. The genes or gene constructs can either be present in plasmids having differing copy numbers or be integrated, and amplified, in the chromosome. Alternatively, it is also possible to achieve overexpression of the genes concerned by altering the composition of the medium and the conduct of the culture.

In general, the amplification, in particular over-expression, measures which are taken increase the activity or concentration of the corresponding protein by at least 10%, 25%, 50%, 75%, 100%, 150%, 200%, 300%, 400% or 500%, and maximally up to 1000% or 2000%, based on that of the wild-type protein or on the activity or concentration of the protein in microorganisms which are not transformed with the nucleotide sequences according to the invention.

The invention also relates to the provision of vectors which are in general autonomously replicatable in the selected host strains, which are compatible with each other and which contain at least nucleotide sequences as claimed in claims 2, 3 and 4 or a nucleotide sequence as claimed in claim 4.

Vector DNA can be introduced into eukaryotic or prokaryotic cells using known transformation techniques.

The host organisms employed are preferably microorganisms, such as *Pseudomonas, Pichia*, various yeasts, *Saccaromyces, Aspergillus* or the family *Streptomyces*, in particular *E. coli*, for which expression systems are existing. Microorganisms of the genus *Rhodococcus* are also suitable.

The invention also relates to a process for preparing nitrile hydratase originating from *Rhodococcus*, especially *Rhodococcus opacus* or microorganisms comprising this enzyme, in which a) a transformed microorganism, which comprises over-expressed genes having the nucleotide sequences as claimed in claims 1 to 4, is fermented in the presence of from 0.15 to 4 mM (mmol/l) $Co^{2+}$, in particular from 0.3 to 4 mM, under conditions which lead to the formation of the nitrile hydratase, b) this enzyme is allowed to accumulate in the micro-organism, and c) this enzyme is isolated from the cells, or d) the microorganisms are harvested and isolated as resting cells which comprise the enzyme.

The recombinantly produced nitrile hydratase converts α-aminonitriles with an activity of >50 U/mg of dry biomass.

The fermentation is preferably carried out in the presence of from 0.5 to 3.5 mM $Co^{2+}$, in particular of from 0.7 to 3 mM, which is preferably added to the fermentation broth as soluble salt.

The microorganisms which are used in accordance with the invention can be cultured continuously or discontinuously, in a batch process or a fed batch process or a repeated fed batch process. A summary of known culturing methods is given in the textbook by Chmiel (Bioprozeβtechnik 1. Einfuhrüng in die Bioverfahrenstechnik [Bioprocess technology 1. Introduction to bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Braunschweig/Wiesbaden, 1994)).

The culture medium which is to be used must suitably satisfy the requirements of the given strains.

Descriptions of media for culturing different micro-organisms are to be found in the manual "Manual of Methods for General Bacteriology" published by the American Society for Bacteriology (Washington D.C., USA, 1981).

Carbon sources which can be used are sugars and carbohydrates, such as glucose, sucrose, lactose, fructose, maltose, molasses, starch and cellulose, oils and fats, such as soybean oil, sunflower oil, peanut oil and coconut oil, fatty acids, such as palmitic acid, stearic acid and linoleic acid, alcohols, such as glycerol and ethanol, and organic acids, such as acetic acid. These substances can be used individually or as mixtures.

Nitrogen sources which can be used are nitrogen-containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate. The nitrogen sources can be used individually or as mixtures.

The phosphorus sources used can be phosphoric acid, potassium dihydrogen phosphate or dipotassium hydrogen phosphate or the corresponding sodium-containing salts. The culture medium has furthermore to contain metal salts, such as magnesium sulfate or iron sulfate, which are required for growth. Finally, it is possible to employ essential growth substances, such as amino acids and vitamins, in addition to the abovementioned substances. The abovementioned added substances can be added to the culture in the form of a once-only mixture or fed in, in a suitable manner, during the culture.

Basic compounds, such as sodium hydroxide, potassium hydroxide, ammonia or ammonia water, or acidic compounds, such as phosphoric acid or sulfuric acid, are used, in a suitable manner, for controlling the pH of the culture. Antifoamants, such as fatty acid polyglycol esters, can be used for controlling foam formation. Suitable substances which act selectively, such as antibiotics, can be added to the medium, in order to maintain the stability of plasmids. Oxygen and oxygen-containing gas mixtures, such as air, are passed into the culture in order to maintain aerobic conditions. The temperature of the culture is normally from 10° C. to 40° C. and preferably from 10° C. to 30° C. The culture is preferably continued at least until it has passed through the logarithmic phase of growth. This objective is normally achieved within from 10 hours to 70 hours.

The invention also relates to a process for enzymically preparing amides from nitrites, which comprises the following steps:

a) converting a nitrile group-containing compound using a *Rhodococcus*, especially *Rhodococcus opacus* enzyme which exhibits nitrile hydratase activity, and b) where appropriate, separating off the amide.

In one process variant, the cells are harvested, washed and taken up, as a suspension, in a buffer at a pH of 5-9, in particular of from 6.8 to 7.9. The concentration of the resting cells is generally 1-25%, in particular from 1.5 to 15% (wet weight/v). The cells can be permeabilized using physical or chemical methods, for example toluene as described in Wilms et al., J. Biotechnol., Vol 86 (2001), 19-30, such that the nitrile compounds which are to be transformed can penetrate through the cell wall and the resulting amide can escape.

The biocatalyst (whole-cell catalyst) is outstandingly stable, such that product concentrations of more than 100 g/l can be achieved.

It is also possible to use known methods to separate off the nitrile hydratase according to the invention from the cells and, where appropriate, purify it and use it for converting the nitrites.

The invention also relates to a process which is characterized in that compounds of the general formulae

in which:

X: is OH, H, alkyl having from 1 to 4 C atoms, aryl, or, in particular, $NH_2$;

R: is H, saturated alkyl radical having from 1 to 12 C atoms, branched or unbranched, optionally substituted by $NH_2$, alkenyl radicals having from 1 to 12 C atoms, branched or unbranched, cycloalkyl groups having from 3 to 6 C atoms, alkylthio group-substituted alkylene radicals, where alkyl in this case corresponds to a $C_1$ to $C_3$ radical and alkylene corresponds to a bivalent $C_3$ to $C_8$ radical, R': is H, or alkyl having from 1 to 3 C atoms, R": is a mononuclear or binuclear aromatic ring, which possesses from 6 to 12 C atoms and which is optionally substituted by one or two alkyl groups (C1-C3) or Cl or F.

Alkylnitrile having from 1 to 6 C atoms.

are converted into the corresponding amides.

The following nitriles are preferably converted:

saturated mononitriles:

acetonitrile, propionitrile, butyronitrile, isobutyronitrile, valeronitrile, isovaleronitrile and capronitrile, saturated dinitriles:

malonitrile, succinonitrile, glutaronitrile and adiponitrile, aromatic unsubstituted and substituted mononitriles and dinitriles:

benzonitrile, 2,6-difluorobenzonitrile, phthalonitrile, isophthalonitrile and terephthalonitrile, α-aminonitriles:

α-aminopropionitrile, α-aminomethylthiobutyronitrile, α-aminobutyronitrile, aminoacetonitrile, all nitrites derived from natural amino acids, α-amino-3,3-dimethylpropionitrile and α-amino-2,3-dimethylpropionitrile nitriles containing carboxyl groups:

cyanoacetic acid

β-aminonitriles:

3-aminopropionitrile unsaturated nitrites:

acrylonitrile, methacrylonitrile, allyl cyanide and crotonormitrile

α-hydroxynitriles:

α-hydroxy-n-propionitrile, α-hydroxy-n-butyronitrile, α-hydroxyisobutyronitrile, α-hydroxy-n-hexanonitrile, α-hydroxy-n-heptyronitrile, α-hydroxy-n-octanonitrile, α,γ-dihydroxy-β,β-dimethylbutyronitrile, acrolein cyanohydrin, methacrylaldehyde cyanohydrin, 3-chlorolactonitrile, 4-methylthio-α-hydroxybutyronitrile and α-hydroxy-α-phenylpropionyl.

The concentration, in the reaction solution, of the nitrites to be converted is not restricted to specific ranges.

In order to avoid the enzyme activity being inhibited by the substrate, the concentration of the nitrile is in general kept to from 0,001 to 10 w/w %, in particular from 0.1 to 2 w/w %, based on the quantity of the biocatalyst as dried cell mass. All of the substrate can be added at the beginning of the reaction or the substrate can be added continuously or discontinuously during the reaction.

A solubilizer can be added if the solubility of the nitrile compound in the aqueous reaction system is too low.

However, as an alternative, the reaction can also be carried out in a water/organic solvent two-phase system.

When cells of the microorganism are used as enzymically active material, the ratio of the quantity of the cells employed to the substrate quantity is preferably from 0.001 to 8 w/w % as dried cell mass.

The dry weight of the cell mass is determined using an MA45 Moisture Analyser (Sartorius).

It is also possible to use well-known techniques to immobilize the isolated enzyme and then to employ the enzyme in this form.

The reaction is generally carried out at temperatures of from −5° C. to 50° C., in particular of from 0° C. to 30° C., and over a period of from 0.1 to 100 hours.

The pH of the reaction mixture which is to be maintained is not restricted to specific values as long as the enzymic activity is not impaired. After the reaction, the amide which has been formed can, in a known manner, be separated out of the reaction solution and purified.

The invention also relates to a process in which the amide, or the solution containing the amide, is, for example, separated off from the cells of the biomass and the amide is either hydrolyzed to give the corresponding acid or converted into the corresponding salts of the acid in the added presence of alkali metal or alkaline earth metal hydroxides. Preference is given to MHA-amide being hydrolyzed with calcium hydroxide and the corresponding calcium salt being isolated.

EXAMPLES

Example 1

Cloning the *Rhodococcus opacus* Nitrile Hydratase

*Rhodococcus opacus* chromosomal DNA was digested with the restriction enzymes PinAI, PstI and XmaI (Roche) and the fragments were separated on a 0.8% agarose gel. Standard methods (e.g. in Sambrook et al.: Molecular Cloning, A Laboratory Manual, Cold Spring Habor Laboratory Press, 1989) were used to carry out a Southern blot onto a positively charged nylon membrane (Hybond-N+, Amersham). Hybridization was carried out with a DIG-labeled probe in accordance with the manufacturer's (Roche) instructions. The probe was prepared by means of PCR using the degenerate primers 1F and 1R and employing genomic DNA as a template. The primers were derived from homologous regions of the β subunit, with these regions being determined by aligning the sequences of various NHases. Their sequences were obtained from databases. In order to isolate a detected PinAI fragment of approx. 2.2 kb in size, PinAI-cut DNA fragments of between 2 and 2.5 kb were purified by means of preparative gel electrophoresis and ligated into the XmaI-cut vector pUC18 (Promega), and the ligation mixture was transformed into *E. coli* JM109 (Promega). Positive transformants were identified by means of colony hybridization using the same probe. The clones which were obtained in this way contained a 2206 nt insert comprising the gene for the β subunit, and the majority of the gene for the α subunit, of the nitrile hydratase.

In order to obtain the missing sequence, the above-described method, employing the primers 2F and 2R, was used to prepare a new probe which hybridized at the 3' end of the cloned PinAI fragment. The PinAI fragment cloned into pUC18 served as template. Prior to hybridizing with this probe, the color signals, and the first probe, were first of all removed from the above-described membrane in accordance with the manufacturer's (Roche) instructions. A PstI band of approx. 2 kb in size was detected on this membrane using the second probe. As described above, the corresponding DNA fragment was cloned into the vector pUC18, which had been opened with PstI, and the product was transformed into *E. coli* JM109; positive clones were then identified by means of colony hybridization. The PstI fragment is 1883 nt in size and contains a (3') part of the gene for the α subunit of the nitrile hydratase, the gene for the auxiliary protein P15K and a (5') part of the gene for the cobalt transporter.

In order to clone a DNA fragment containing the missing sequence of the cobalt transporter gene, the primers 3F and 3R, and the PstI fragment cloned in pUC18, with this fragment serving as template, were used to prepare a new probe which hybridized at the 3' end of the cloned PstI fragment. This probe was used to detect an XmaI band of approx. 1.7 kb in size on the same membrane, from which color signals and the second probe had in turn been previously removed. The corresponding DNA fragment was cloned into the pUC18 vector, which had been opened with XmaI, and the product was transformed into *E. coli* JM109; positive clones were identified by means of colony hybridization. A probe which had been amplified using the primers 4F and 3R was used for this purpose. The XmaI fragment is 1747 nt in size and contains a (3') part of the gene for the cobalt transporter.

The continuous sequence of the gene cluster, which contains the polynucleotides encoding the α and β subunits of the nitrile hydratase, the auxiliary protein P15K and the cobalt transporter, is depicted in SEQ ID NO:1.

Example 2

Constructing the Expression Vectors

The structural genes were cloned into an expression vector which is known for being used in *E. coli* and in which the inserted genes are under the control of a rhamnose promoter. A second rhamnose promoter was inserted in addition. To achieve this, the gene for the β subunit was amplified using the primers 5F and 5R, which inserted cleavage sites for the restriction enzymes NdeI, BamHI and HindIII. The second rhamnose promoter was amplified using the primers 6F and 6R, which inserted the cleavage sites for the restriction enzymes BamHI, NcoI and HindIII. The gene for the α subunit was amplified using the primers 7F and 7R, which inserted cleavage sites for the restriction enzymes NcoI, KpnI and HindIII. The gene for the P15K protein was amplified using the primers 8F and 8R, which inserted the cleavage sites for the restriction enzymes KpnI and HindIII and altered the start codon from GTG to ATG. The expression vector which was constructed in this way is designated pUD 15.

The restriction map is given in FIG. 1, while the sequence is given in SEQ ID NO:24.

The gene for the cobalt transporter was cloned into another E. coli expression vector in which the inserted genes are also under the control of the rhamnose promoter. For this, the cobalt transporter gene was amplified using the primers 9F and 9R, which inserted the cleavage sites for the restriction enzymes NdeI and HindIII and altered the start codon from TTG to ATG. The expression vector which was constructed in this way is designated pUD 16.

The restriction map is given in FIG. 2, while the sequence is given in SEQ ID NO:25.

The expression plasmids were transformed into the E. coli strain DSM 14459, which is deposited in the Deutschen Sammlung von Mikroorganismen and Zellkulturen [German collection of microorganisms and cell cultures] GmbH (DSMZ).

Primers:

```
1F  5'-ATG AAY GGH ATY TTC GA-3'

1R  5'-ATC CAG TGY YHG TAG TA-3'

2F  5'-CGA AGA CAT GAT CGT CGT G-3'

2R  5'-ACC GGT CCC ACA CCG A-3'

3F  5'-TCG AGG AGA TCG GAG G-3'

3R  5'-GTA TCG AAG GTG CTC ATC-3'

4F  5'-CGC GGG CTG GGT GAA-3'

5F  5'-CGG CGG AAT TCA AGA AGG AGA CCC GCA TAT GAA
    CGG-3'

5R  5'-GGT GCA AGC TTGGAT CCT GTC AGA TTC CTC GAG
    TAG-3'

6F  5'-GCG AAG GAT CCT GCA TGC ATC GAA ATT AAT
    ACG-3'

6R  5'-CAT CAA GCT TTT CGC CAT GGC TAT ATC TCC
    TTC-3'

7F  5'-CTG ACA GGA TCC AAG AAG GAG ATA TAG CCA TGG
    CCG A-3'

7R  5'-GTT GCA AGC TTG GTA CCG CTC AAG ACA TCG CCT
    CCC T-3'

8F  5'-GTG GGT ACC AAG AAG GAG GCG ATC ATA TGA GCA
    CGC-3'

8R  5'-GCG GAC GAG TAG CGA AGC TTG TTA GTT CAC
    CG-3'

9F  5'-TCA AAG CTT GAA GGA GAT ATA CAT ATG ACG ATT
    ACT-3'

9R  5'-GTC AAG CTT GGT ACC GAC ATC TCA CAC CTT
    CGA-3'
```

The genes are located on the segments:

| pUD15: | gene for the β subunit: | nt | 25-732 |
|---|---|---|---|
|  | gene for the α subunit: | nt | 949-1566 |
|  | P15K gene: | nt | 1592-2005 |
| pUD16: | gene for the cobalt transporter: | nt | 25-1095 |

Example 3

Heterologous Expression of the Nitrile Hydratase in E. coli DSM 14559

DSM 14559 was deposited in connection with DE 101 55 928.

The pUD15-transformed cells were grown, at 37° C. and while shaking, in LB medium (LB broth in accordance with Miller, VWR) which contained 1 mM $CoCl_2$ and 100 µg of ampicillin/ml. The cells transformed with pUD15 and pUD16 were grown in an analogous manner but with the medium additionally containing 50 µg of chloramphenicol/ml. After that, the cells were inoculated over into the same medium 3 times after they had reached an $OD_{600}$ of at least 2. After 12-16 hours, a quantity of the last preliminary culture was inoculated over into a main culture such that this latter had an $OD_{600}$ of 0.1. While the culture medium for the main culture corresponded to that for the preliminary culture, it additionally contained 2 g of L-rhamnose/l. The cells were harvested after 22 hours.

Example 4

Determining the Enzymic Activity

The cells were grown as described in example 3, separated off from the culture medium by centrifugation and resuspended in standard buffer (50 mM potassium phosphate buffer, pH 7.5). 50 µl of this cell suspension were added to 700 µl of the standard buffer and 250 µl of a 200 mM solution of the nitrile in standard buffer were added to start the reaction. In this connection, the concentration of the cells in the cell suspension was gauged such that 5-30% of the nitrile had reacted after 10 min at 20° C. After 10 min at 20° C., the reaction was stopped by adding 20 µl of half-concentrated phosphoric acid and the cells were separated off by centrifugation.

| HPLC analysis | |
|---|---|
| Column | Intersil ODS-3V |
| Mobile phase | Mixture composed of 10 mM potassium phosphate buffer, pH 2.3, and acetonitrile in a ratio of 85:15 in the case of methionine nitrile, MHA-nitrile and acetocyanohydrin and of 99:1 in the case of all the other substrates |
| Flow rate | 1 ml/min |
| Detection | UV at 200 nm |

The activity of one unit (U) was defined as the quantity of enzyme which converts 1 µmol of N-formylvaline nitrile to the amide in one minute. The specific activity is given in U per mg of dry biomass (U/mg of DBM).

This is measured using a model MA45 Moisture Analyser (Sartorius).

Example 5

Coexpressing the genes encoding the nitrile hydratase α subunit, the β subunit and the p15K protein.

The expression was carried out as described in example 3 using the transformed E. coli strain DSM 14459, which harbored plasmid pUD15. The specific activity of the cells was 23 U/mg of DBM.

Example 6

Coexpressing the genes encoding the nitrile hydratase α subunit, the β subunit, the p15K protein and the cobalt transporter.

The expression was carried out as described in example 3 using the transformed *E. coli* strain DSM 14459 harboring plasmids pUD15 and pUD16. The specific activity of the cells was 81 U/mg of DBM.

Example 7

Substrate Specificity

Various nitriles were converted, in analogy with example 3, using resting transformed *E. coli* DSM 14459 cells which harbored plasmid pUD15. The specific activity which was obtained with N-formylvaline nitrile was set as being equal to 100%. The other activities were given in relation to it. The results are depicted in FIG. 3.

Example 8

Growth of Transformed *E. coli* DSM 14459 in the Presence of Co2+Salts

Transformed *E. coli* DSM 14459 cells, which harbored either only plasmid pUD15 or pUD15 and pUD16, were grown as described in example 3. At the same time, the cobalt concentration in the medium was varied from 0.5 to 2 mM. After 24 hours, the optical densities of the cultures were measured at 600 nm.

|  | *E. coli* harboring pUD15 | *E. coli* harboring pUD15 and pUD16 |
|---|---|---|
| 0.5 mM CoCl2 | 2.808 | 2.524 |
| 1.0 mM CoCl2 | 2.6955 | 2.173 |
| 2.0 mM CoCl2 | 2.330 | 2.113 |

It is found that it is only possible to observe a slight influence on the growth of the cells even at high cobalt concentrations.

Example 9

Converting methionine nitrile using resting transformed *E. coli* DSM 14459 cells which harbor plasmid pUD15.

*E. coli* DSM 14459 cells which harbored plasmid pUD15 were grown, and centrifuged down, as described in example 3. 2.8 g of the cells, based on the wet weight, were resuspended in 47.2 ml of 50 mM potassium phosphate buffer, pH 7.5, and methionine nitrile was added continuously, at 20° C. and while agitating vigorously, at a rate which was such that the concentration did not exceed 15 g/l at any time during the reaction. The pH was maintained constant at 7.5. The reaction was monitored by means of HPLC, as described in example 4. After 320 min, 9.1 g of the nitrile had been completely converted into 10.4 g of amide. This corresponds to a concentration of 176 g/l.

Figure 1:
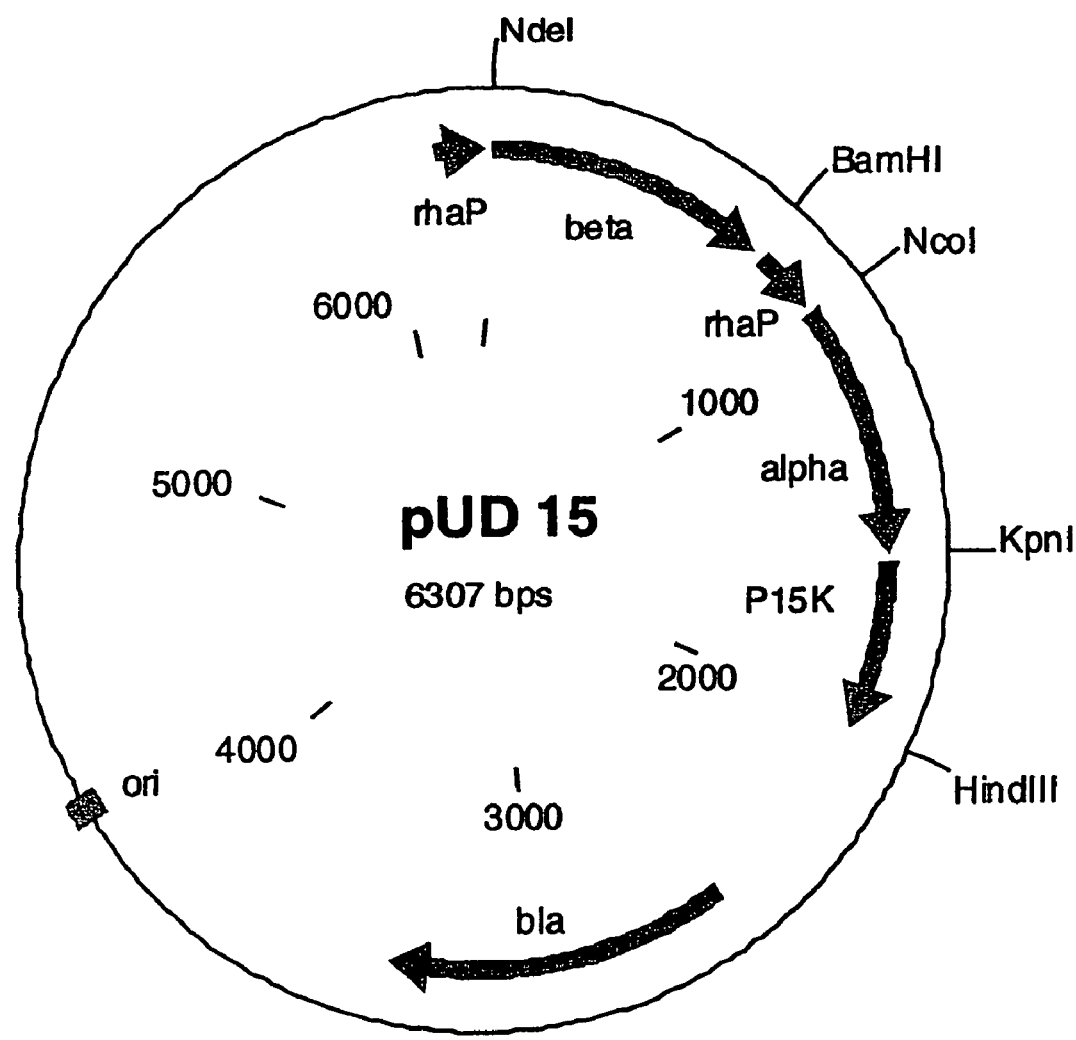
FIG. 1
Figure 2:
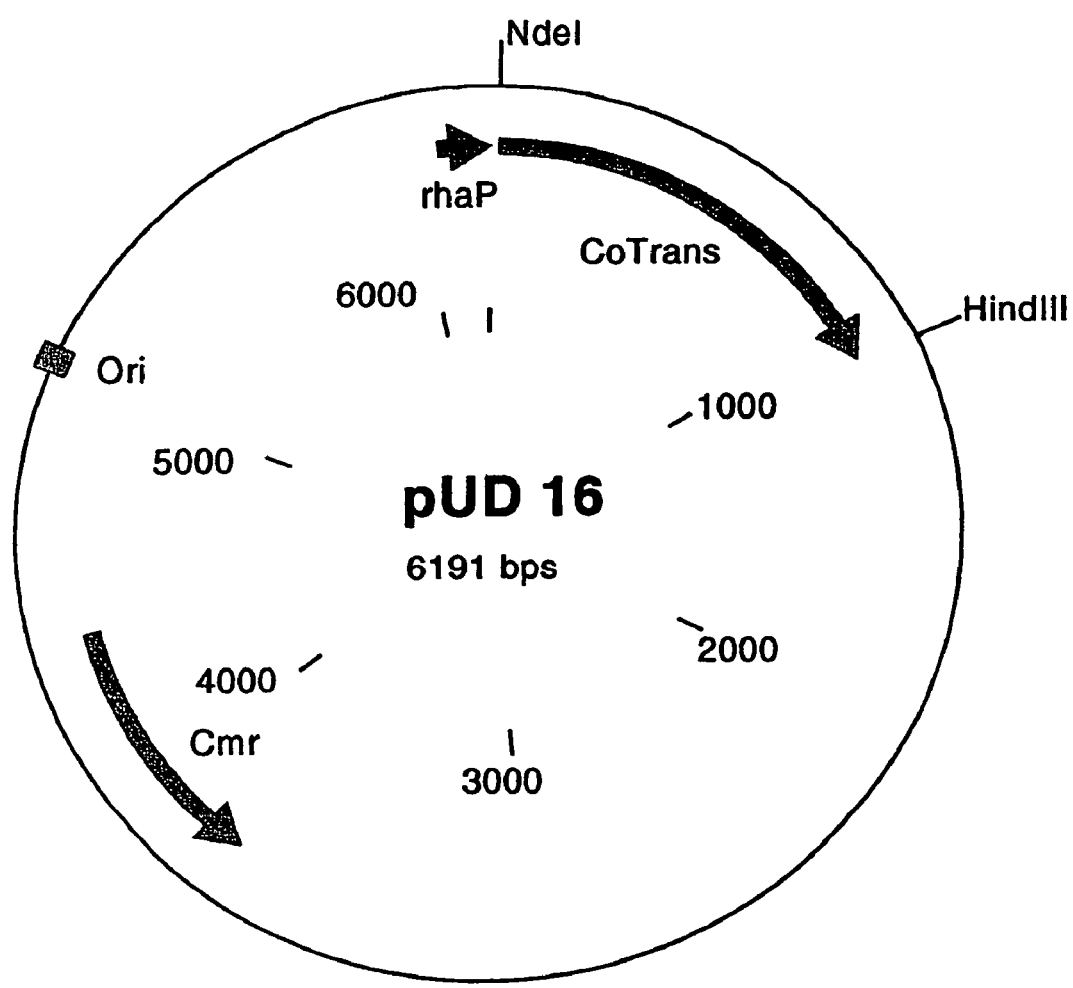
Figure 3:
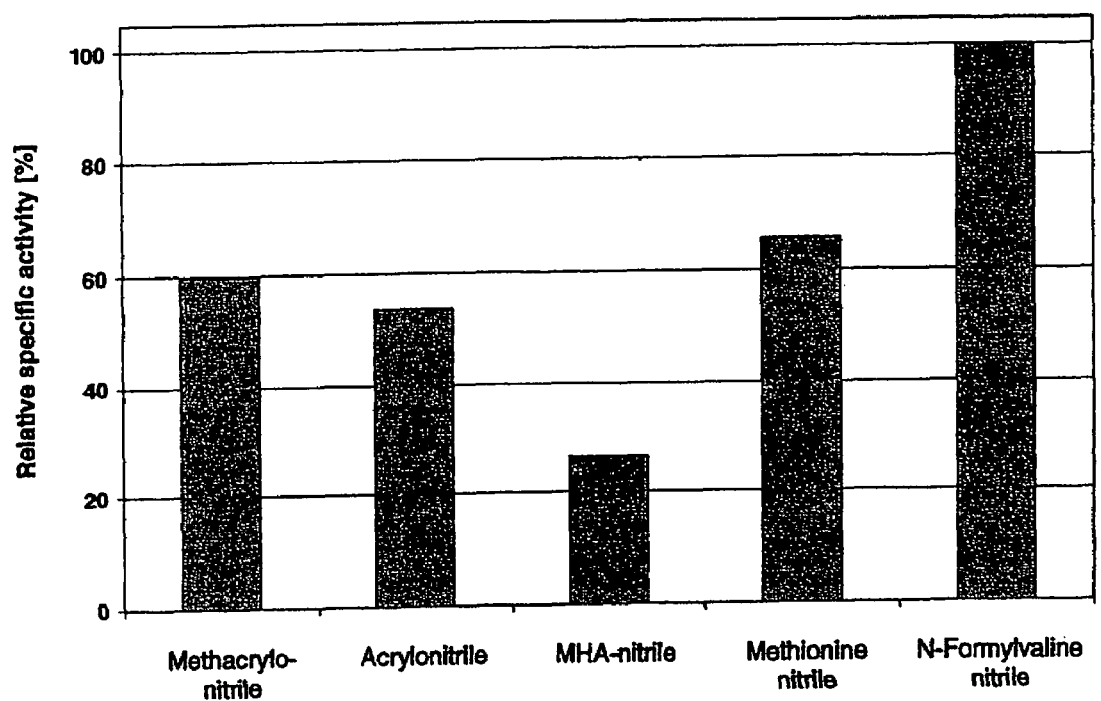

| Plasmid pUD15 | |
|---|---|
| rhaP | rhamnose promoter |
| beta | gene for the nitrile hydratase β subunit |
| alpha | gene for the nitrile hydratase α subunit |
| P15K | gene for the auxiliary protein P15K |
| ori | origin of replication |
| bla | gene for resistance to ampicillin (β-lactamase) |

FIG. 2

| Plasmid pUD16 | |
|---|---|
| rhaP | rhamnose promoter |
| CoTrans | gene for the cobalt transporter |
| ori | origin of replication |
| Cmr | gene for resistance to chloramphenicol |

Relative specific activity when converting various nitriles in comparison with the activity when converting N-formylvaline nitrile.

---

The invention claimed is:

1. A process for enzymatically preparing an amide from a nitrile comprising:
   a) converting a nitrile group-containing compound using a with transformed microorganism transformed with a vector expressing a nitrile hydratase enzyme having:
      i) a beta subunit with an amino acid sequence that is at least 95% identical to that of SEQ ID NO:2; and
      ii) an alpha subunit at least 95% identical to the sequence SEQ ID NO:3; and
   b) purifying said amide.

2. The process of claim 1, wherein said beta subunit comprises the amino acid sequence of SEQ ID NO:2 and said alpha subunit comprises the amino acid sequence of SEQ ID NO:3.

3. The process of claim 1, wherein said beta subunit consists of the amino acid sequence of SEQ ID NO:2 and said alpha subunit consists of the amino acid sequence of SEQ ID NO:3.

4. The process of claim 1, wherein said nitrile hydratase converts α-aminonitriles with a specific activity of > 50 U/mg of dry biomass.

5. The process of claim 1, wherein resting cells which comprise said nitrile hydratase are used.

6. The process of claim 1, wherein a nitrile of the general formula

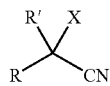

(I)

is converted into the corresponding amide and in which:
   X is OH, H, an alkyl having from 1 to 4 carbon atoms or $NH_2$;
   R is H; a branched or unbranched saturated alkyl radical having from 1 to 12 carbon atoms and optionally substituted with $NH_2$; a branched or unbranched alkenyl radical having from 1 to 12 carbon atoms; a cycloalkyl group having from 3 to 6 C atoms; an alkylthio group-substituted alkylene radical, wherein said alkyl is a $C_1$ to $C_3$ radical and said alkylene is a bivalent $C_3$ to $C_8$ radical;
   R' is H, or an alkyl having from 1 to 3 with carbon atoms, and which is optionally substituted by one or two $C_1$ to $C_3$ alkyl groups or Cl, Br or F, or a monovalent alkylnitrile radical having from 1 to 6 carbon atoms.

7. The process of claim 1, wherein said nitrile is methionine nitrile.

8. The process of claim 6, wherein said beta subunit comprises the amino acid sequence of SEQ ID NO:2 and said alpha subunit comprises the amino acid sequence of SEQ II) NO:3.

9. The process of claim 8, wherein said nitrile is methionine nitrile.

10. The process of claim 6, wherein said beta subunit consists of the amino acid sequence of SEQ ID NO:2 and said alpha subunit consists of the amino acid sequence of SEQ ID NO:3.

11. The process of claim 10, wherein said nitrile is methionine nitrile.

12. The process of claim 6, wherein R and $R_1$ are H.

13. The process of claim 12, wherein X is OH.

14. The process of claim 12, wherein X is an alkyl having from 1 to 4 carbon atoms.

15. The process of claim 12, wherein X is $NH_2$.

16. The process of claim 6, wherein R is a branched or unbranched saturated alkyl radical having from 1 to 12 carbon atoms and optionally substituted with $NH_2$.

17. The process of claim 16, wherein X is an alkyl having from 1 to 4 carbon atoms.

18. The process of claim 16, wherein X is $NH_2$.

19. The process of claim 6, wherein R is a cycloalkyl group having from 3 to 6 C atoms.

20. The process of claim 19, wherein X is an alkyl having from 1 to 4 carbon atoms.

* * * * *